US009226850B2

(12) United States Patent
Baerveldt et al.

(10) Patent No.: US 9,226,850 B2
(45) Date of Patent: *Jan. 5, 2016

(54) MINIMALLY INVASIVE GLAUCOMA SURGICAL INSTRUMENT AND METHOD

(71) Applicant: The Regents of the University of California, Oakland, CA (US)

(72) Inventors: George Baerveldt, Monarch Beach, CA (US); Roy Chuck, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 132 days.

This patent is subject to a terminal disclaimer.

(21) Appl. No.: 13/850,231

(22) Filed: Mar. 25, 2013

(65) Prior Publication Data

US 2013/0289545 A1   Oct. 31, 2013

Related U.S. Application Data

(63) Continuation of application No. 12/843,458, filed on Jul. 26, 2010, now Pat. No. 8,512,321, which is a continuation of application No. 11/273,914, filed on Nov. 14, 2005, now Pat. No. 7,785,321, which is a (Continued)

(51) Int. Cl.
*A61B 18/18* (2006.01)
*A61F 9/007* (2006.01)
(Continued)

(52) U.S. Cl.
CPC .............. *A61F 9/00781* (2013.01); *A61F 9/008* (2013.01); *A61F 9/00745* (2013.01); *A61F 9/00802* (2013.01); *A61F 9/00825* (2013.01);
(Continued)

(58) Field of Classification Search
CPC ... A61F 9/008; A61F 9/00781; A61F 9/0079; A61F 9/00825; A61F 2009/0087; A61F 2009/00885; A61F 2009/00887; A61F 2009/00891; A61B 18/18; A61B 18/20; A61B 2018/1425
USPC ............ 606/4–6, 10, 32, 41–50, 167; 607/96, 607/98–105; 128/898
See application file for complete search history.

(56) References Cited

U.S. PATENT DOCUMENTS

| 590,681 A | 9/1897 | Harthan |
| 2,850,007 A | 9/1958 | Lingley |

(Continued)

FOREIGN PATENT DOCUMENTS

| EP | 0 898 947 A2 | 3/1999 |
| WO | WO 98/30157 A1 | 7/1998 |

(Continued)

OTHER PUBLICATIONS

Aida Excimer laser for Excimer Laser Trabeculotomy. Catalog. Unknown publication date, but predates invention.

(Continued)

*Primary Examiner* — Ahmed Farah
(74) *Attorney, Agent, or Firm* — Kilpatrick Townsend & Stockton LLP

(57) ABSTRACT

Apparatuses and methods for the treatment of glaucoma are provided. The instrument uses either cauterization, a laser to ablate, sonic or ultrasonic energy to emulsify, or mechanical cutting of a portion of the trabecular meshwork. The instrument may also be provided with irrigation, aspiration, and a footplate. The footplate is used to enter Schlemm's canal, serves as a guide, and also protects Schlemm's canal.

28 Claims, 37 Drawing Sheets

Related U.S. Application Data continuation of application No. 10/052,473, filed on Jan. 18, 2002, now Pat. No. 6,979,328.

(60) Provisional application No. 60/263,617, filed on Jan. 18, 2001.

(51) Int. Cl.
*A61F 9/008* (2006.01)
*A61B 17/32* (2006.01)
*A61B 18/14* (2006.01)

(52) U.S. Cl.
CPC ..... *A61B 17/320068* (2013.01); *A61B 18/1477* (2013.01); *A61B 2017/320072* (2013.01); *A61B 2018/1425* (2013.01); *A61F 9/0079* (2013.01); *A61F 2009/00844* (2013.01); *A61F 2009/00868* (2013.01); *A61F 2009/00891* (2013.01)

(56) References Cited

U.S. PATENT DOCUMENTS

| | | | |
|---|---|---|---|
| 3,007,471 A | 11/1961 | McClure, Jr. | |
| 3,583,390 A | 6/1971 | Jascalevich | |
| 3,844,272 A | 10/1974 | Banko | |
| 3,893,445 A | 7/1975 | Hofsess | |
| 3,929,123 A | 12/1975 | Jamshidi | |
| 3,996,935 A | 12/1976 | Banko | |
| 4,011,869 A | 3/1977 | Seiler, Jr. | |
| 4,041,947 A | 8/1977 | Weiss et al. | |
| 4,282,884 A | 8/1981 | Boebel | |
| 4,301,802 A | 11/1981 | Poler | |
| 4,308,875 A | 1/1982 | Young | |
| 4,320,761 A | 3/1982 | Haddad | |
| 4,481,948 A | 11/1984 | Sole | |
| 4,501,274 A | 2/1985 | Skjaerpe | |
| 4,538,611 A | 9/1985 | Kelman | |
| 4,559,942 A | 12/1985 | Eisenberg | |
| 4,570,632 A | 2/1986 | Woods | |
| 4,577,629 A | 3/1986 | Martinez | |
| 4,590,935 A | 5/1986 | Ranalli | |
| 4,674,499 A | 6/1987 | Pao | |
| 4,689,040 A | 8/1987 | Thompson | |
| 4,694,828 A | 9/1987 | Eichenbaum | |
| 4,805,616 A | 2/1989 | Pao | |
| 4,846,172 A | 7/1989 | Berlin | |
| 4,900,300 A | 2/1990 | Lee | |
| 4,955,883 A | 9/1990 | Nevyas et al. | |
| 5,025,811 A | 6/1991 | Dobrogowski et al. | |
| 5,074,861 A | 12/1991 | Schneider et al. | |
| 5,123,902 A | 6/1992 | Muller et al. | |
| 5,129,895 A | 7/1992 | Vassiliadis et al. | |
| 5,133,714 A | 7/1992 | Beane | |
| 5,135,295 A | 8/1992 | Jen et al. | |
| 5,163,433 A | 11/1992 | Kagawa et al. | |
| 5,178,604 A | 1/1993 | Baerveldt et al. | |
| 5,324,282 A | 6/1994 | Dodick | |
| 5,360,399 A | 11/1994 | Stegmann | |
| 5,370,641 A | 12/1994 | O'Donnell, Jr. | |
| 5,407,443 A | 4/1995 | Kobayashi et al. | |
| 5,431,646 A | 7/1995 | Vassiliadis et al. | |
| 5,437,678 A | 8/1995 | Sorensen | |
| 5,472,440 A | 12/1995 | Beckman | |
| 5,488,165 A | 1/1996 | Hutchin et al. | |
| 5,549,598 A | 8/1996 | O'Donnell, Jr. | |
| 5,591,160 A | 1/1997 | Reynard | |
| 5,688,261 A | 11/1997 | Amirkhanian et al. | |
| 5,722,970 A | 3/1998 | Colvard et al. | |
| 5,733,256 A | 3/1998 | Costin | |
| 5,738,676 A | 4/1998 | Hammer et al. | |
| 5,738,677 A | 4/1998 | Colvard et al. | |
| 5,743,871 A | 4/1998 | Strukel | |
| 5,755,716 A | 5/1998 | Garito et al. | |
| 5,788,679 A | 8/1998 | Gravlee, Jr. | |
| 5,825,958 A | 10/1998 | Gollihar et al. | |
| 5,830,209 A | 11/1998 | Savage et al. | |
| 5,833,643 A | 11/1998 | Ross et al. | |
| 5,865,831 A | 2/1999 | Cozean et al. | |
| 5,871,492 A | 2/1999 | Sorensen | |
| 5,893,849 A | 4/1999 | Weaver | |
| 5,893,862 A | 4/1999 | Pratt et al. | |
| 5,906,611 A | 5/1999 | Dodick et al. | |
| 5,957,921 A | 9/1999 | Mirhashemi et al. | |
| 5,958,266 A | 9/1999 | Fugo et al. | |
| 5,972,416 A | 10/1999 | Reimels et al. | |
| 5,980,548 A | 11/1999 | Evans et al. | |
| 5,989,249 A | 11/1999 | Kirwan, Jr. | |
| 6,004,318 A | 12/1999 | Garito et al. | |
| 6,007,555 A | 12/1999 | Devine | |
| 6,013,049 A | 1/2000 | Rockley et al. | |
| 6,059,772 A | 5/2000 | Hsia et al. | |
| 6,083,193 A | 7/2000 | Kadziauskas et al. | |
| 6,086,583 A | 7/2000 | Ouchi | |
| 6,096,031 A | 8/2000 | Mitchell et al. | |
| 6,117,149 A | 9/2000 | Sorensen | |
| 6,126,629 A | 10/2000 | Perkins | |
| 6,135,998 A | 10/2000 | Palanker | |
| 6,135,999 A | 10/2000 | Fanton et al. | |
| 6,140,740 A | 10/2000 | Porat et al. | |
| 6,142,990 A | 11/2000 | Burk | |
| 6,142,996 A | 11/2000 | Mirhashemi et al. | |
| 6,220,247 B1 | 4/2001 | Maldonado Bas | |
| 6,228,084 B1 | 5/2001 | Kirwan, Jr. | |
| 6,241,721 B1 * | 6/2001 | Cozean et al. | 606/6 |
| 6,251,103 B1 * | 6/2001 | Berlin | 606/15 |
| 6,319,274 B1 | 11/2001 | Shadduck | |
| 6,325,792 B1 | 12/2001 | Swinger et al. | |
| 6,352,535 B1 | 3/2002 | Lewis et al. | |
| 6,406,476 B1 | 6/2002 | Kirwan, Jr. et al. | |
| 6,524,275 B1 | 2/2003 | Lynch et al. | |
| 6,533,408 B1 | 3/2003 | Erdtmann et al. | |
| 6,626,890 B2 | 9/2003 | Nguyen et al. | |
| 6,638,239 B1 | 10/2003 | Bergheim et al. | |
| 6,733,491 B2 | 5/2004 | Kadziauskas et al. | |
| 6,979,328 B2 | 12/2005 | Baerveldt et al. | |
| 7,094,200 B2 | 8/2006 | Katzman | |
| 7,182,759 B2 | 2/2007 | Kadziauskas et al. | |
| 7,785,321 B2 | 8/2010 | Baerveldt et al. | |
| 2002/0072673 A1 | 6/2002 | Yamamoto et al. | |
| 2003/0181909 A1 | 9/2003 | Kirwan, Jr. | |
| 2003/0208217 A1 | 11/2003 | Dan | |
| 2004/0082939 A1 | 4/2004 | Berlin | |

FOREIGN PATENT DOCUMENTS

| | | |
|---|---|---|
| WO | WO 99/51156 A1 | 10/1999 |
| WO | WO 00/64389 A1 | 11/2000 |
| WO | WO 00/64390 A1 | 11/2000 |
| WO | WO 00/67687 A1 | 11/2000 |

OTHER PUBLICATIONS

Bayraktar, S., et al., "Endoscopic Goniotomy with Anterior Chamber Maintainer: Surgical Technique and One-Year Results," *Ophthalmic Surg Lasers* Nov.-Dec.; 32(6):496-502, 2001.

"Cautery pens reduce scleral shrinkage," *Ophthalmology Times*, p. 51, Aug. 15, 2000.

Charters, Lynda, "Erbium: YAG Laser Effective for Vitreoretinal Surgery," *Ophthalmology Times*, p. 68, Jun. 15, 2000.

Dietlein T.S., et al., "Erbium; YAG Laser Trabecular Ablation (LTA)in the Surgical Treatment of Glaucoma," *Lasers Surg Med* 23(2) 104-10, 1998.

Dietlein, T.S., et al., "Ab Inferno Infrared Laser Trabecular Ablation: Preliminary Short-Term Results in Patients with Open-Angle Glaucoma," *Graefes Arch Clin Exp Ophthalmol.*, 235(6), 349-353, 1997.

Dynamic Surgery, Cautery Probes, www.dynamicsurgery.com; ClearSight Cautery Probes, 4 pages.

Endo-Optiks; www.endo-optiks.com; "Using the Technology; Endoscopic Direct-View Goniotomy," 1 page.

Gayton, Johnny L., M.D., "A Smart Bomb for Glaucoma Treatment?" http://www.endo-optiks.com/a smrtbm.htm; 4 pages.

(56) References Cited

OTHER PUBLICATIONS

Hill, Richard A., et al., "Effects of Pulse Width on Erbium: YAG Laser Photothermal Trabecular Ablation LTA)," *Lasers in Surgery and Medicine* 13:440-446, 1993.

Hill, Richard A., et al., "Laser Trabecular Ablation(LTA)," *Lasers in Surgery and Medicine*, 11:341-346, 1991.

Hofmann, A., et al., "Radiowave Surgery Case Report," *International Journal of Aesthatic and Restorative Surgery*, 4:131-133, 2000.

HS. International Co., Inc., Ophthalmic Micro-surgical Instruments. Catalog. Unknown publication date, but predate invention.

Jacobi, P.C., et al., "Experimental Microendoscopic Photoablative Laser Goniotomy as a Surgical Model for the Treatment of Dysgenetic Glaucoma," *Graefes Arch Clin Exp. Ophthalmol* 234(1):670-676, 2000.

Jacobi, P.C., et al., "Microendoscopic Trabecular Surgery in Glaucoma Management," *Ophthalmology* 106(3) 538-44, 1999.

Katana Eye Instruments. Catalog, p. 142. Unknown publication date, but predates invention.

Maldonado-Bas A. et al., "Filtering Glaucoma Surgery Using an Excimer Laser," *J Cataract Refract Surg.* 27(9) 1402-9, 2001.

Mandicino, M.E., "Long-term Surgical and Visual Outcomes in Primary Congenital Glaucoma: 360 Degrees Trabeculotomy Versus Goniotomy," *J. AAPOS* 4(4): 205-210, 2000.

Maselli et al., "Diathermo-Trabeculotomy Ab Externo: A New Technique for Opening the Canal of Schlemm," *Brit. J. Ophthal.* 59: 516 (1975).

Maselli et al., "Diathermo-Trabeculotomy Ab Externo: Indications and Long Term Results," *Brit. J. Ophthal.* 61: 675-676 (1977).

McHugh, Josh; "The Electromagnetic Scalpel", *Forbes Magazine*, Oct. 5, 1998, 5 pages.

Microsurgery Advanced Design Lab. www.madlab.ihu.edu/manhan.htm. Initiatives, 1 page.

Millennium TSV25 System, Transconjunctival Standard Virectomy. Brochure from Bausch & Laumb, Copyright 2001.

Newton, Casey, "Procedure Helps Correct Farsightedness," Newspaper Article from The Orange County Register, Oct. 4, 2000.

Ophthalmology Times. Unknown publication date, but predates invention date.

Rhein Medical Inc. Advertisement. Unknown publication date, but publication predates invention.

Skjaerpe, F., "Selective Trabeculectomy a Report of a New Surgical Method for Open Angle Glaucoma," *ACTA Ophthalmologica* 61:714-727, 1983.

Storz Ophthalmics, Catalog, pp. 144, 205. Unknown publication date, but predates invention.

Sun, W., et al., "Endoscopic Gonioitomy with the Free Electron laser in Congenital Glaucoma Rabbits," *J. Glaucoma* 9(4):325-333, 2000.

Surgitron, EMC, Catalog, Unknown publication date, but predates invention.

The C.V. Mosby Co., St. Louis, Mo.; Retina vol. 3, Chapter 124, pp. 192-195, 1989.

The Foundation of the American Academy of Ophthalmology. Basic and Clinical Science Course. pp. 85-91.

* cited by examiner

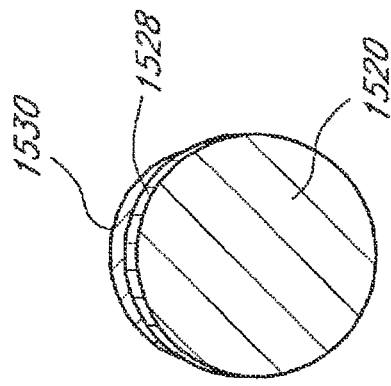
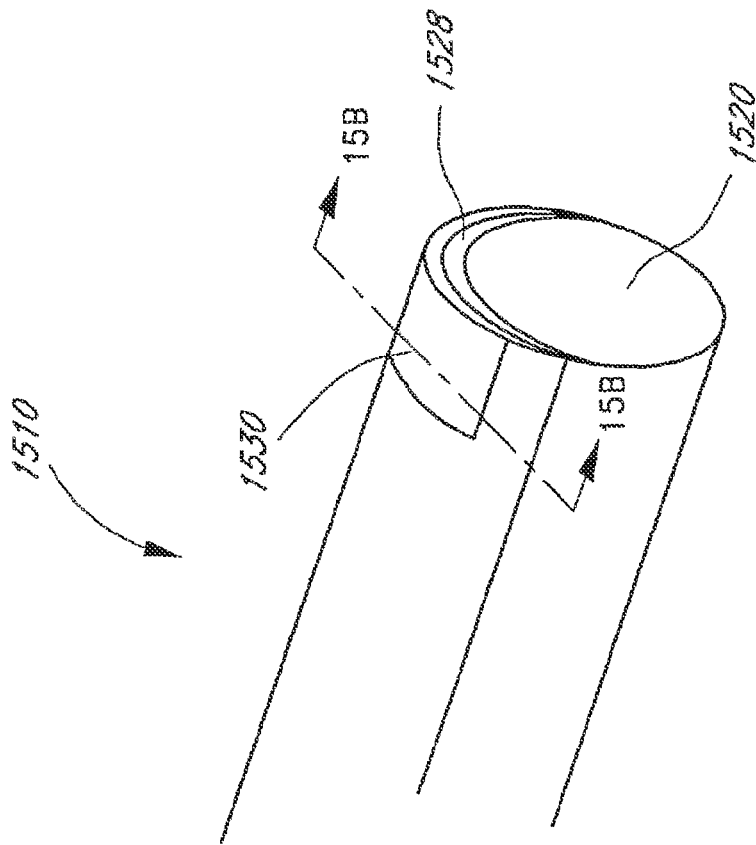
FIG. 15B
FIG. 15A

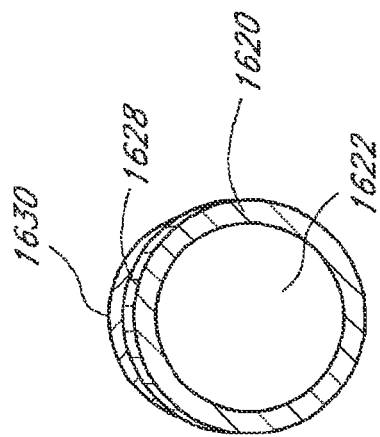
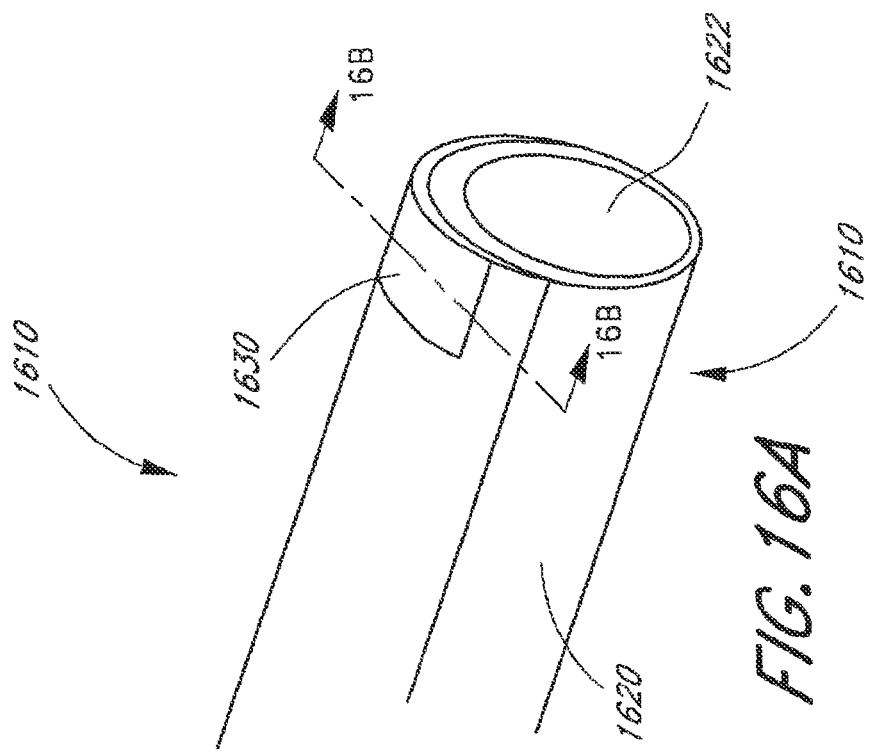

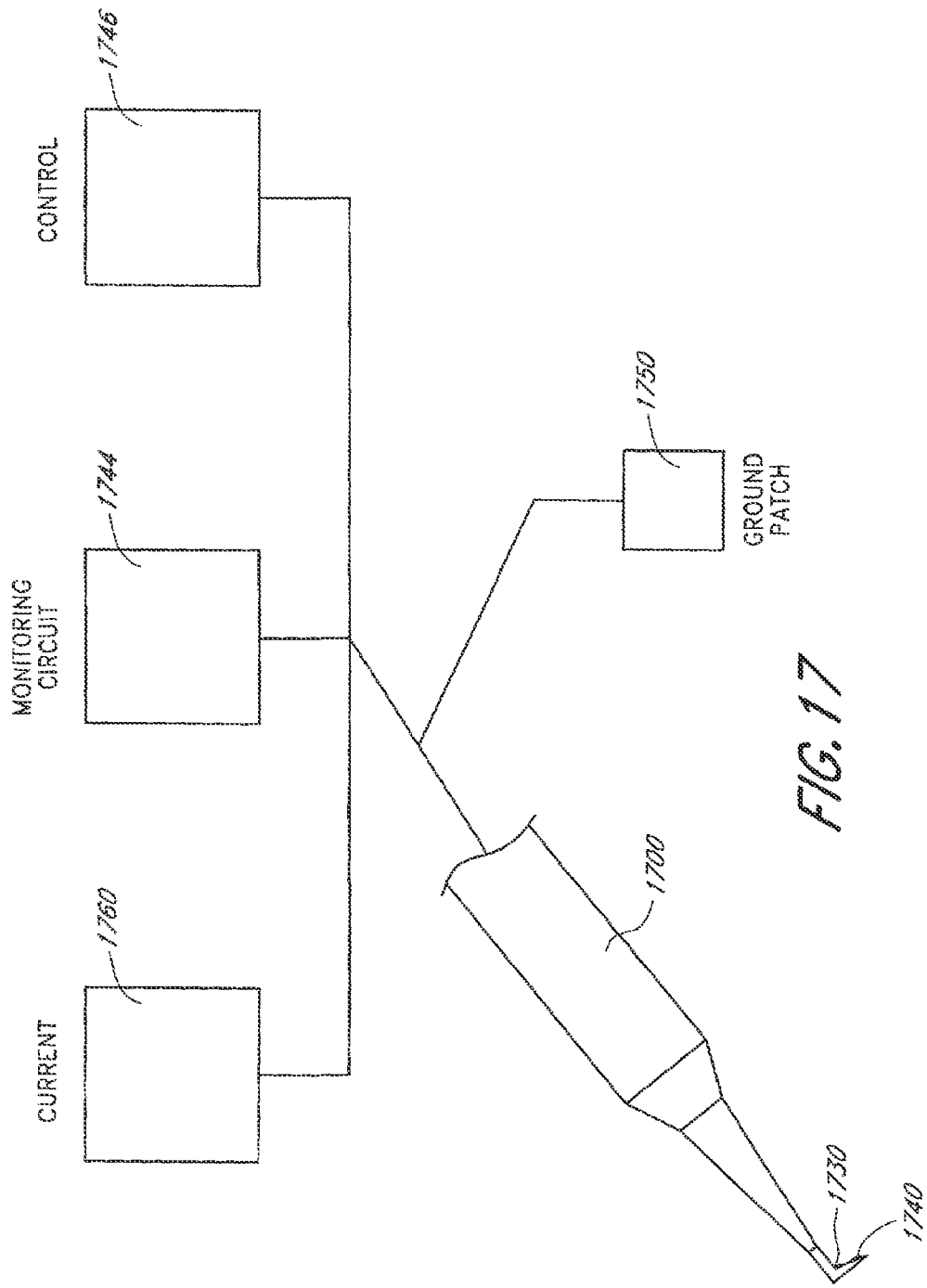

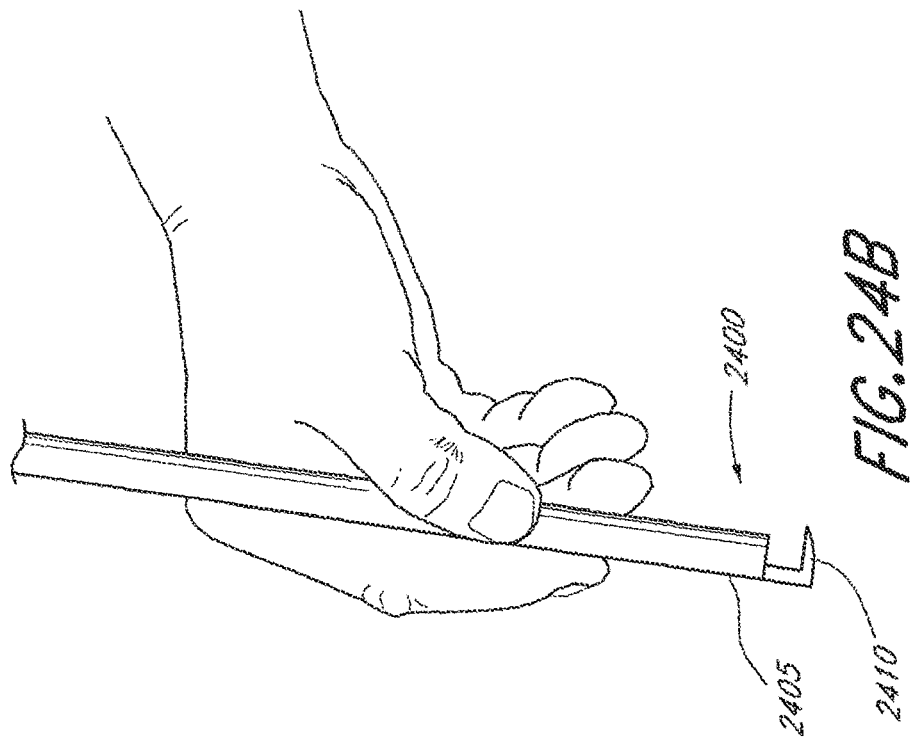
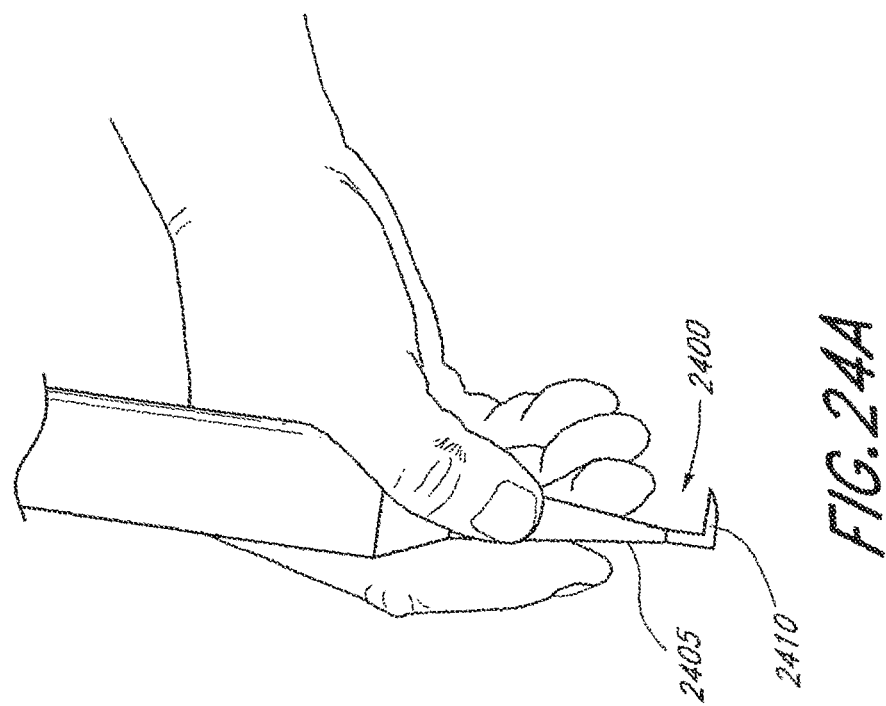

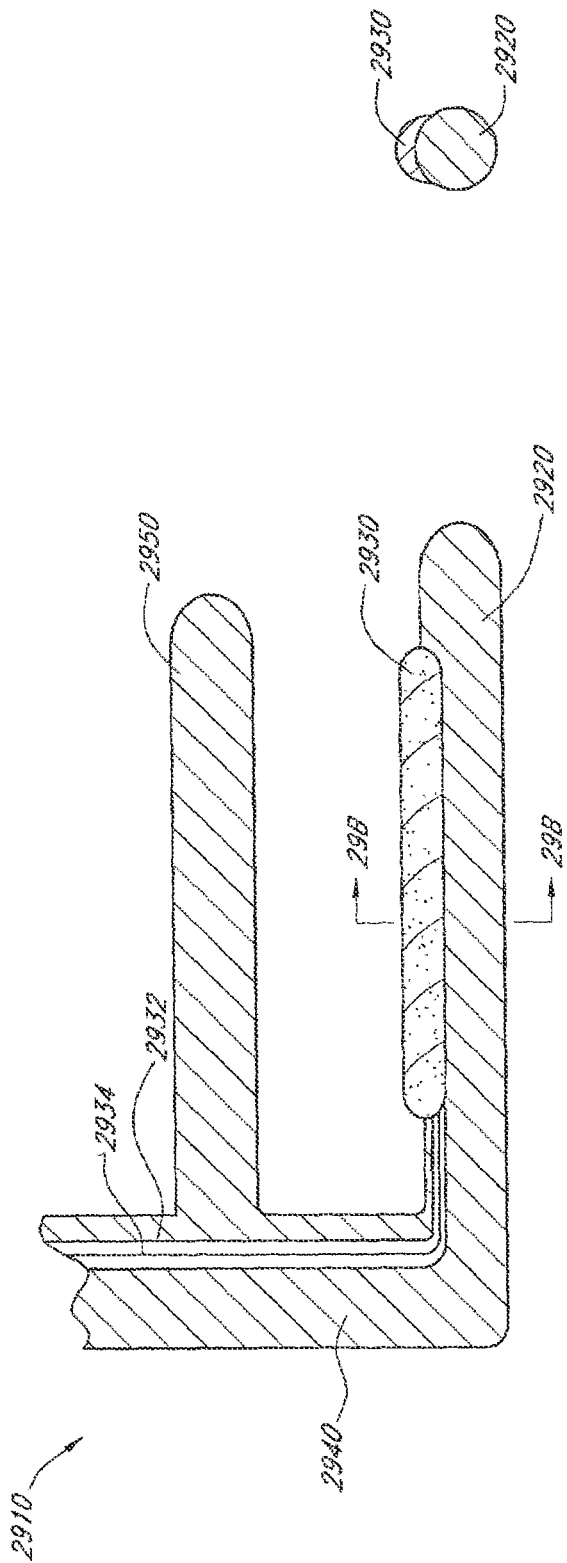
FIG. 29A
FIG. 29B
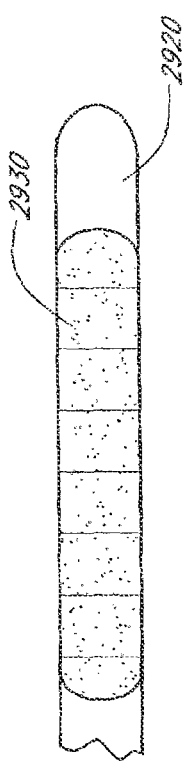
FIG. 29C

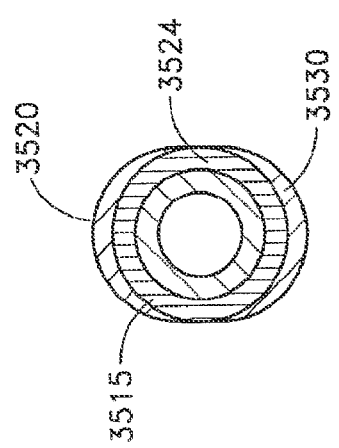
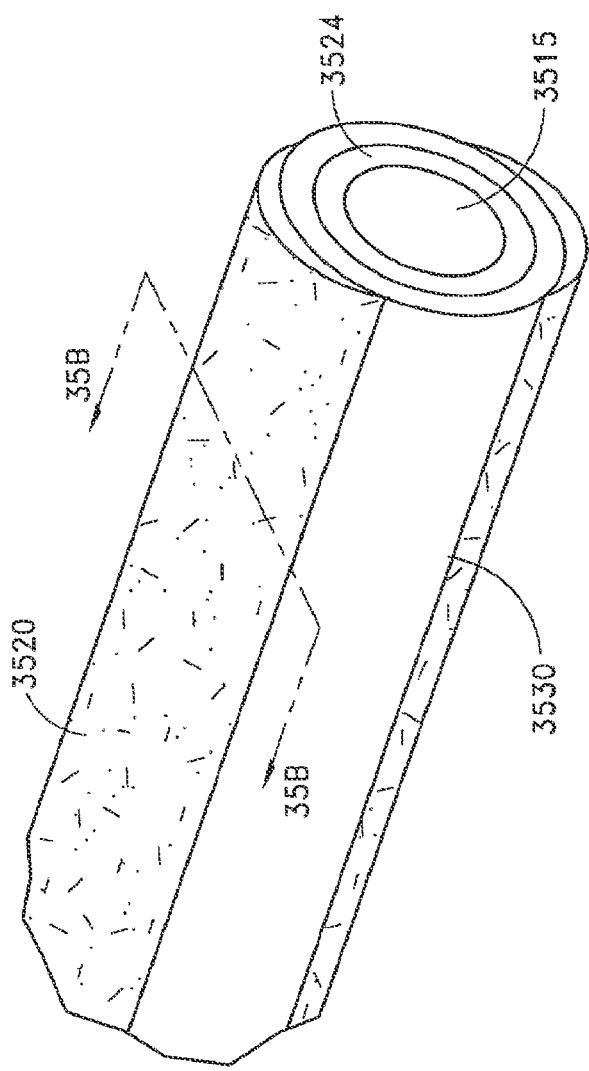

MINIMALLY INVASIVE GLAUCOMA SURGICAL INSTRUMENT AND METHOD

CROSS-REFERENCES TO RELATED APPLICATIONS

This application is a continuation of U.S. patent application Ser. No. 12/843,458, filed Jul. 26, 2010, which is a continuation of U.S. patent application Ser. No. 11/273,914, filed Nov. 14, 2005, now U.S. Pat. No. 7,785,321, which is a continuation of U.S. patent application Ser. No. 10/052,473, filed Jan. 18, 2002, now U.S. Pat. No. 6,979,238, which claimed priority to U.S. Provisional Application Ser. No. 60/263,617, filed Jan. 18, 2001, the full disclosures of which are herein incorporated by reference in their entirety.

BACKGROUND OF THE INVENTION

1. Field of the Invention

The present invention relates to a new glaucoma surgical instrument and method, and, in particular, removal of the trabecular meshwork by mechanical cautery, vaporization or other tissue destruction means optionally coupled to an instrument with infusion, aspiration, and a footplate.

2. Description of the Related Art

Aqueous is a clear, colorless fluid that fills the anterior and posterior chambers of the eye. The aqueous is formed by the ciliary body in the eye and supplies nutrients to the lens and cornea. In addition, the aqueous provides a continuous stream into which surrounding tissues can discharge the waste products of metabolism.

The aqueous produced in the ciliary process circulates from the posterior chamber to the anterior chamber of the eye through the pupil and is absorbed through the trabecular meshwork, a plurality of crisscrossing collagen cords covered by endothelium. Once through the trabecular meshwork, the aqueous passes through Schlemm's canal into collector channels that pass through the scleral and empty into the episcleral venous circulation. The rate of production in a normal eye is typically 2.1 µL/min. Intraocular pressure in the eye is maintained by the formation and drainage of the aqueous. All the tissues within the corneoscleral coat covering the eyeball are subject to this pressure, which is higher than pressure exerted on tissues at other locations in the body.

Glaucoma is a group of diseases characterized by progressive atrophy of the optic nerve head leading to visual field loss, and ultimately, blindness. Glaucoma is generally associated with elevated intraocular pressure, which is an important risk factor for visual field loss because it causes further damage to optic nerve fibers. Other causes of glaucoma may be that the nerve is particularly vulnerable to the pressure due to poor local circulation, tissue weakness or abnormality of structure. In a "normal" eye, intraocular pressure ranges from 10 to 21 mm mercury. In an eye with glaucoma, this pressure can rise to as much as 75 mm mercury.

There are several types of glaucoma, including open and closed angle glaucoma, which involve the abnormal increase in intraocular pressure, primarily by obstruction of the outflow of aqueous humor from the eye, or, less frequently, by over production of aqueous humor within the eye. The most prevalent type is primary open angle glaucoma in which the aqueous humor has free access to the irridocorneal angle, but aqueous humor drainage is impaired through obstruction of the trabecular meshwork. In contrast, in closed angle glaucoma, the irridocorneal angle is closed by the peripheral iris. The angle block can usually be corrected by surgery. Less prevalent types of glaucoma include secondary glaucomas related to inflammation, trauma, and hemorrhage.

Aqueous humor is similar in electrolyte composition to plasma, but has a lower protein content. The aqueous humor keeps the eyeball inflated, supplies the nutritional needs of the vascular lens and cornea and washes away metabolites and toxic substances within the eye. The bulk of aqueous humor formation is the product of active cellular secretion by nonpigmented epithelial cells of the ciliary process from the active transport of solute, probably sodium, followed by the osmotic flow of water from the plasma. The nonpigmented epithelial cells of the ciliary process are connected at their apical cell membranes by tight junctions. These cells participate in forming the blood/aqueous barrier through which blood-borne large molecules, including proteins, do not pass.

Intraocular pressure (IOP) is a function of the difference between the rate at which aqueous humor enters and leaves the eye. Aqueous humor enters the posterior chamber by three means: 1) active secretion by nonpigmented epithelial cells of the ciliary process; 2) ultrafiltration of blood plasma; and 3) diffusion. Newly formed aqueous humor flows from the posterior chamber around the lens and through the pupil into the anterior chamber; aqueous humor leaves the eye by 1) passive bulk flow at the irridocorneal angle by means of the uveloscleral outflow, or by 2) active transportation through the trabecular meshwork, specifically the juxta canalicar portion. Any change in 1), 2), or 3) will disturb aqueous humor dynamics and likely alter intraocular pressure.

Primary open angle glaucoma is caused by a blockage in the trabecular meshwork. This leads to an increase in intraocular pressure. The major obstruction is at the juxta-canalicular portion which is situated adjacent to Schlemm's canal. In infants a goniotomy or a trabeculotomy can be performed. In goniotomy or trabeculotomy a small needle or probe is introduced into Schlemm's canal and the trabecular meshwork is mechanically disrupted into the anterior chamber. Approximately 90°-120° of trabecular meshwork can be disrupted. The anatomical difference between congenital glaucoma and adult glaucoma is that in congenital glaucoma the ciliary body muscle fibers insert into the trabecular meshwork and once disrupted the trabecular meshwork is pulled posteriorly allowing fluid to enter Schlemm's canal and to be removed through the normal collector channels that are present in the wall of Schlemm's canal. In adults the trabecular meshwork tears but remains intact and reattaches to the posterior scleral wall of Schlemm's canal blocking the collector channels.

Most treatments for glaucoma focus on reducing intraocular pressure. Treatment has involved administration of beta-blockers such as timolol to decrease aqueous humor production, adranergic agonists to lower intraocular pressure or diuretics such as acetazolamide to reduce aqueous production, administration of miotic eyedrops such as pilocarpine to facilitate the outflow of aqueous humor, or prostaglandin analogs to increase uveoscleral outflow. Acute forms of glaucoma may require peripheral iridectomy surgery to relieve pressure where drug therapy is ineffective and the patient's vision is at immediate risk. Other forms of treatment have included physical or thermal destruction ("cyclodestruction") of the ciliary body of the eye, commonly by surgery or application of a laser beam, cryogenic fluid or high frequency ultrasound.

In guarded filtration surgery (trabeculectomy), a fistula created through the limbal sclera is protected by an overlying partial thickness sutured scleral flap. The scleral flap provides additional resistance to excessive loss of aqueous humor from the eyeball, thereby reducing the risk of early postoperative hypotony.

In accordance with one recently introduced procedure, a full thickness filtering fistula may be created by a holmium laser probe, with minimal surgically induced trauma. After retrobulbar anesthesia, a conjunctival incision (approximately 1 mm) is made about 12-15 mm posterior to the intended sclerostomy site, and a laser probe is advanced through the sub-conjunctival space to the limbus. Then, multiple laser pulses are applied until a full thickness fistula is created. This technique has sometimes resulted in early hypotony on account of a difficulty in controlling the sclerostomy size. In addition, early and late iris prolapse into the sclerostomy has resulted in abrupt closure of the fistula and eventual surgical failure. Further, despite its relative simplicity, the disadvantage of this procedure, as well as other types of glaucoma filtration surgery, is the propensity of the fistula to be sealed by scarring.

Various attempts have been made to overcome the problems of filtration surgery, for example, by using ophthalmic implant instruments such as the Baerveldt Glaucoma Implant. Typical ophthalmic implants utilize drainage tubes so as to maintain the integrity of the openings formed in the eyeball for the relief of the IOP.

Typical ophthalmic implants suffer from several disadvantages. For example, the implants may utilize a valve mechanism for regulating the flow of aqueous humor from the eyeball; defects in and/or failure of such valve mechanisms could lead to excessive loss of aqueous humor from the eyeball and possible hypotony. The implants also tend to clog over time, either from the inside by tissue, such as the iris, being sucked into the inlet, or from the outside by the proliferation of cells, for example by scarring. Additionally, the typical implant insertion operation is complicated, costly and takes a long time and is reserved for complicated glaucoma problems.

There are many problems, however, in effectively treating glaucoma with long term medicinal or surgical therapies. One problem is the difficulty in devising means to generate pharmacologically effective intraocular concentrations and to prevent extraocular side effects elicited by a systemic administration. Many drugs are administered topically or locally. The amount of a drug that gets into the eye is, however, only a small percentage of the topically applied dose because the tissues of the eye are protected from such substances by numerous mechanisms, including tear turnover, blinking, conjunctival absorption into systemic circulation, and a highly selective corneal barrier.

Pharmacological treatment is prohibitively expensive to a large majority of glaucoma patients. In addition, many people afflicted with the disease live in remote or undeveloped areas where the drugs are not readily accessible. The drugs used in the treatment often have undesirable side effects and many of the long-term effects resulting from prolonged use are not yet known. Twenty-five percent of patients do not use their medications correctly.

Glaucoma is a progressively worsening disease, so that a filtration operation for control of intraocular pressure may become necessary. Present surgical techniques to lower intraocular pressure, when medication fails to decrease fluid flow into the eye or to increase fluid outflow, include procedures that permit fluid to drain from within the eye to extraocular sites by creating a fluid passageway between the anterior chamber of the eye and the potential supra-scleral/sub-Tenon's space, or, alternatively, into or through the Canal of Schlemm (see, e.g., U.S. Pat. No. 4,846,172). The most common operations for glaucoma are glaucoma filtering operations, particularly trabeculectomy. These operations involve creation of a fistula between the subconjunctival space and the anterior chamber. This fistula can be made by creating a hole at the limbus by either cutting out a portion of the limbal tissues with either a scalpel blade or by burning with a cautery through the subconjunctival space into the anterior chamber. Fluid then filters through the fistula and is absorbed by episcleral and conjunctival. In order for the surgery to be effective, the fistula must remain substantially unobstructed. These drainage or filtering procedures, however, often fail by virtue of closure of the passageway resulting from the healing of the very wound created for gaining access to the surgical site. Failures most frequently result from scarring at the site of the incisions in the conjunctiva and the Tenon's capsule. The surgery fails immediately in at least 15% of patients, and long term in a much higher percentage. Presently, this consequence of trabeculectomy, closure of the passageway, is treated with 5-fluorouracil and Mitomycin_C, which apparently prevent closure by inhibiting cellular proliferation. These drugs, however, are highly toxic and have undesirable side effects, including scleral melting, hypotony, leaks, and late infections.

Other surgical procedures have been developed in an effort to treat victims of glaucoma. An iridectomy, removal of a portion of the iris, is often used in angle-closure glaucoma wherein there is an occlusion of the trabecular meshwork by iris contact. Removal of a piece of the iris then gives the aqueous free passage from the posterior to the anterior chambers in the eye. The tissue of the eye can grow back to the pre-operative condition, thereby necessitating the need for further treatment.

In view of the limited effectiveness of treatment options, there is, therefore, a need to develop more effective treatments for glaucoma.

BRIEF SUMMARY OF THE INVENTION

The present invention is a surgical instrument and minimally invasive surgical method to remove at least a portion of the trabecular meshwork of the eye, providing for aqueous drainage in the treatment of glaucoma.

A preferred embodiment of the present invention involves inserting a surgical instrument through a small corneal incision transcamerally under direct visualization to ablate the trabecular meshwork. The instrument may include a foot plate, such that the instrument can penetrate the trabecular meshwork into Schlemm's canal. The footplate may also act as a protective device for the endothelial cells and collector channels lining the scleral wall of Schlemm's canal. The instrument may also comprise an infusion system and aspiration system. Infusion maintains and deepens the anterior chamber so that easy access of the angle of the eye is obtained to the trabecular meshwork and Schlemm's canal. Infusion also allows fluid to flow out to the collector channels whilst the surgery is being performed, thus keeping the surgical site blood free. Aspiration is designed to remove ablated tissue, gas and bubble formation, and all intraocular debris generated. The aspiration may be directly linked to either a cutting mechanism, such as a guillotine cutting machine, laser probe, a piezo-electric crystal producing sonic or ultrasonic energy, or cautery element. These modalities are capable of substantially complete tissue removal by mechanical means, cautery, vaporization, or other tissue destruction techniques.

The surgical instrument is used to perform a goniectomy procedure, by removing a portion of the trabecular meshwork consisting of the pigmented trabecular meshwork, allowing free access of aqueous from the anterior chamber through to the scleral portion of Schlemm's canal that contains the endothelial cells and most importantly the collector channels that lead back to the episcleral venous system.

In another embodiment, a Schlemmectomy surgical procedure, similar to a trabeculotomy, a schlemmectomy probe is inserted into Schlemm's canal under direct visualization through a scleral incision, such that the surface of the instrument faces the trabecular meshwork and the tissue comprising the pigmented and a portion of the nonpigmented trabecular meshwork facing into Schlemm's canal is removed by a cautery element, radio-frequency electrode, or an ultrasound transducer formed from a piezo-electric crystal.

This instrument is advantageous because it combines existing procedures with new technology, providing a simple solution for glaucoma treatment.

BRIEF DESCRIPTION OF THE DRAWINGS

FIG. 15a is a detailed view which shows the probe tip of the goniectomy cautery probe of FIG. 13.

FIG. 15b is a cross-sectional schematic diagram which shows the probe tip of the goniectomy cautery probe of FIG. 13.

FIG. 16a is a detailed view which shows the probe tip of the cautery probe of FIG. 14.

FIG. 16b is a cross-sectional schematic diagram which shows the probe tip of the cautery probe of FIG. 14.

FIG. 17 shows a schematic of a circuit diagram of a preferred embodiment of a goniectomy probe.

FIG. 24a is a perspective view which shows a preferred embodiment of a laser goniectomy probe.

FIG. 24b is a perspective view which shows a preferred embodiment of a laser goniectomy probe.

FIG. 25 is a cross sectional schematic diagram of the laser goniectomy probe of FIG. 24a.

FIGS. 29a-c are detailed views which show the probe tip of the probe of FIG. 28.

FIG. 35a is a detailed view which shows the probe tip of the probe of FIG. 30.

FIG. 35b is a cross-sectional schematic diagram which shows the probe tip of the probe of FIG. 30.

DETAILED DESCRIPTION OF THE INVENTION

Figure 1:
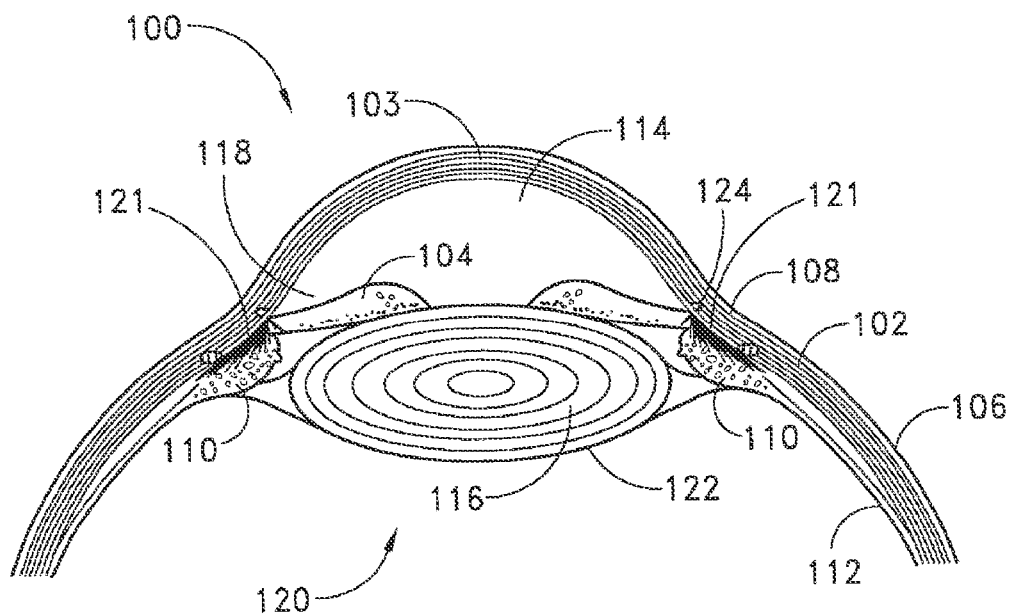
FIG. 1 is a cross sectional schematic diagram of a human eye.

Referring to FIG. 1, relevant structures of the eye will be briefly described, so as to provide background for the anatomical terms used herein. Certain anatomical details, well known to those skilled in the art, have been omitted for clarity and convenience.

As shown in FIG. 1, the cornea 103 is a thin, transparent membrane which is part of the outer eye and lies in front of the iris 104. The cornea 103 merges into the sclera 102 at a juncture referred to as the limbus 108. A layer of tissue called bulbar conjunctiva 106 covers the exterior of the sclera 102. The bulbar conjunctiva 106 is thinnest anteriorly at the limbus 108 where it becomes a thin epithelial layer which continues over the cornea 103 to the corneal epithelium. As the bulbar conjunctiva 106 extends posteriorly, it becomes more substantial with greater amounts of fibrous tissue. The bulbar conjunctiva 106 descends over Tenon's capsule approximately 3 mm from the limbus 108. Tenon's capsule is thicker and more substantial encapsulatory tissue which covers the remaining portion of the eyeball. The subconjunctival and sub-Tenon's capsule space become one when these two tissues meet, approximately 3 mm from the limbus. The ciliary body or ciliary process 110 is part of the uveal tract. It begins at the limbus 108 and extends along the interior of the sclera 102. The choroid 112 is the vascular membrane which extends along the retina back towards the optic nerve. The anterior chamber 114 of the eye is the space between the cornea 103 and a crystalline lens 116 of the eye. The crystalline lens of the eye is situated between the iris 104 and the vitreous body 120 and is enclosed in a transparent membrane called a lens capsule 122. The anterior chamber 114 is filled with aqueous humor 118. The trabecular meshwork 121 removes excess aqueous humor 118 from the anterior chamber 114 through Schlemm's canal 124 into collector channels which merge with blood-carrying veins to take the aqueous humor 118 away from the eye.

Figure 2:
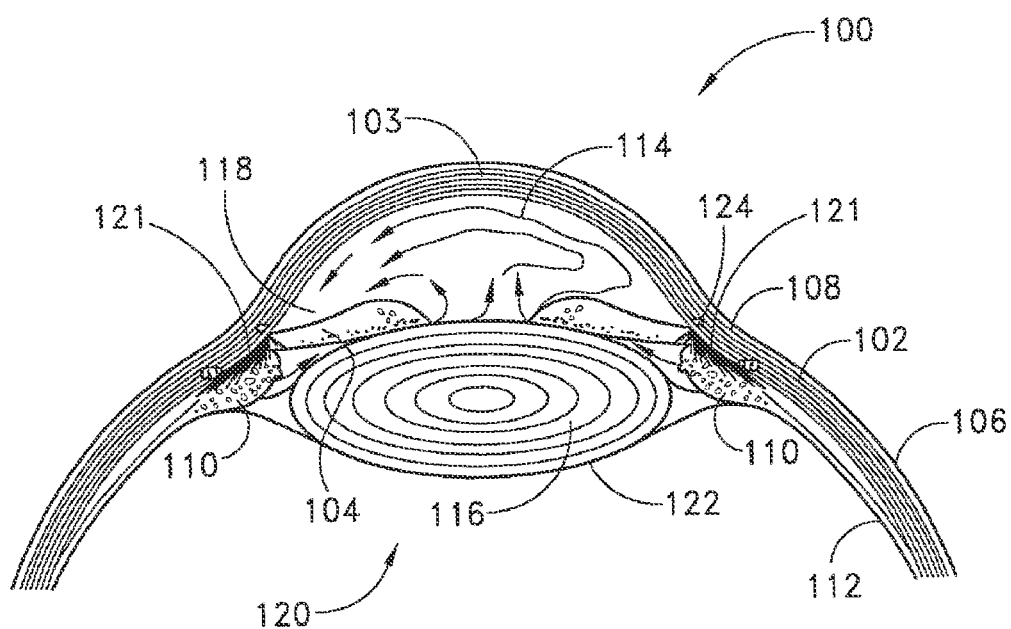
FIG. 2 is a cross sectional schematic diagram which shows aqueous flow into and through the anterior chamber in a human eye.

As shown in FIG. 2, the flow of aqueous 118 is from the posterior chamber, through the pupil, into the anterior chamber 114.

Figure 3A:
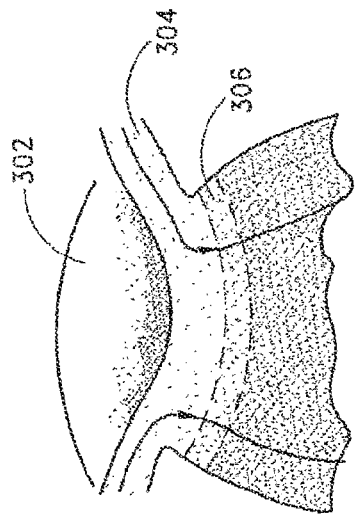
FIGS. 3a-d shows diagrammatically the progression of the deformation of the lamina cribrosa in glaucoma.
Figure 3B:
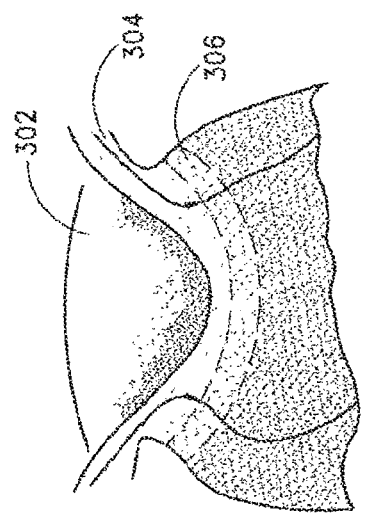
Figure 3C:
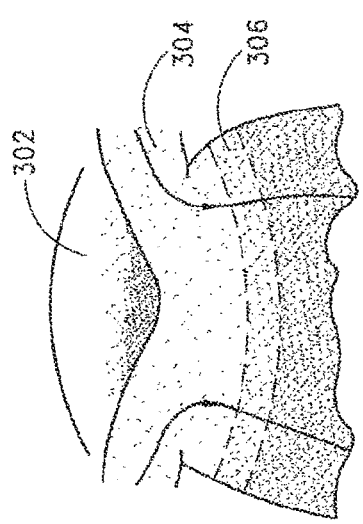
Figure 3D:
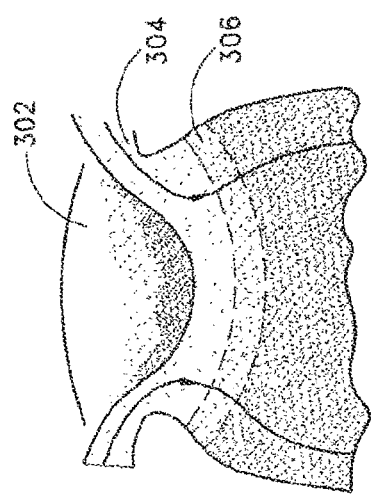

FIGS. 3a-d show longitudinal sections through the optic nerve head, illustrating the progressive deepening of the cup 302 in the nerve head from normal to advanced glaucoma. FIG. 3a shows a normal nerve and FIG. 3d shows an effected nerve in advanced glaucoma. As the cup 302 deepens and the lamina cribrosa 306 becomes more curved, axons 304 passing through the lamina 306 are subject to kinking and pressure as they make their way through the lamina 306.

Goniotomy.

Figure 4A:
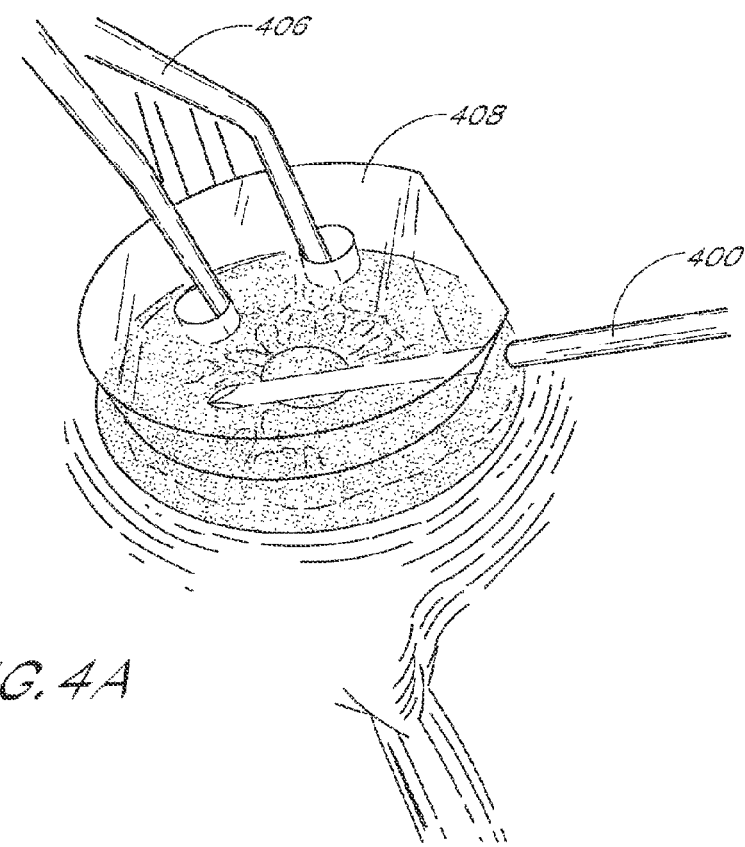
FIGS. 4a-c show diagrammatically the steps of performing a goniectomy.
Figure 4B:
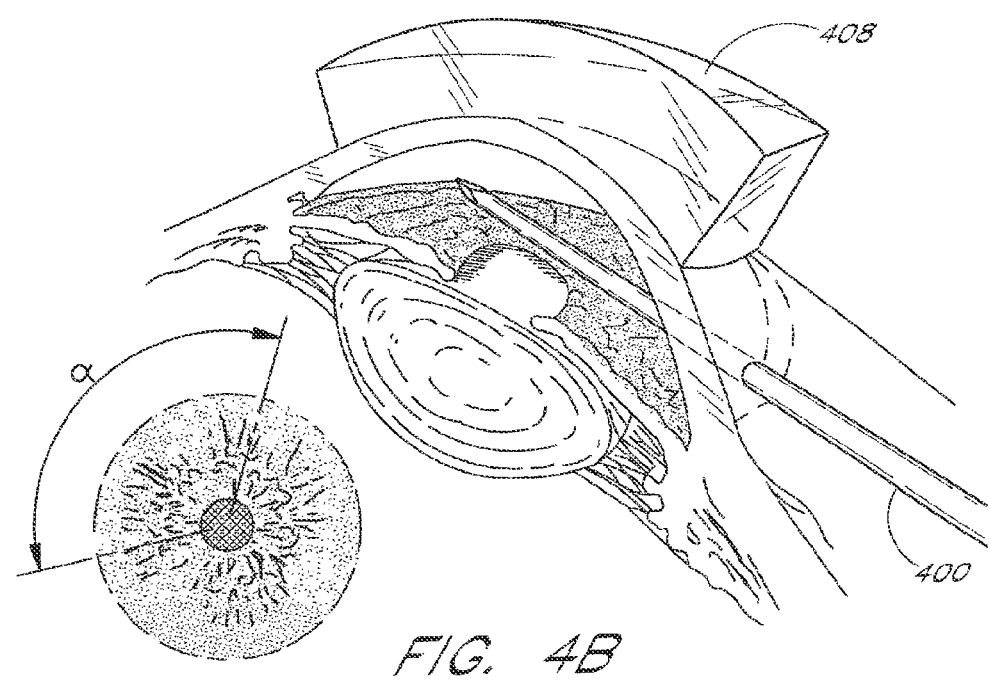
Figure 4C:
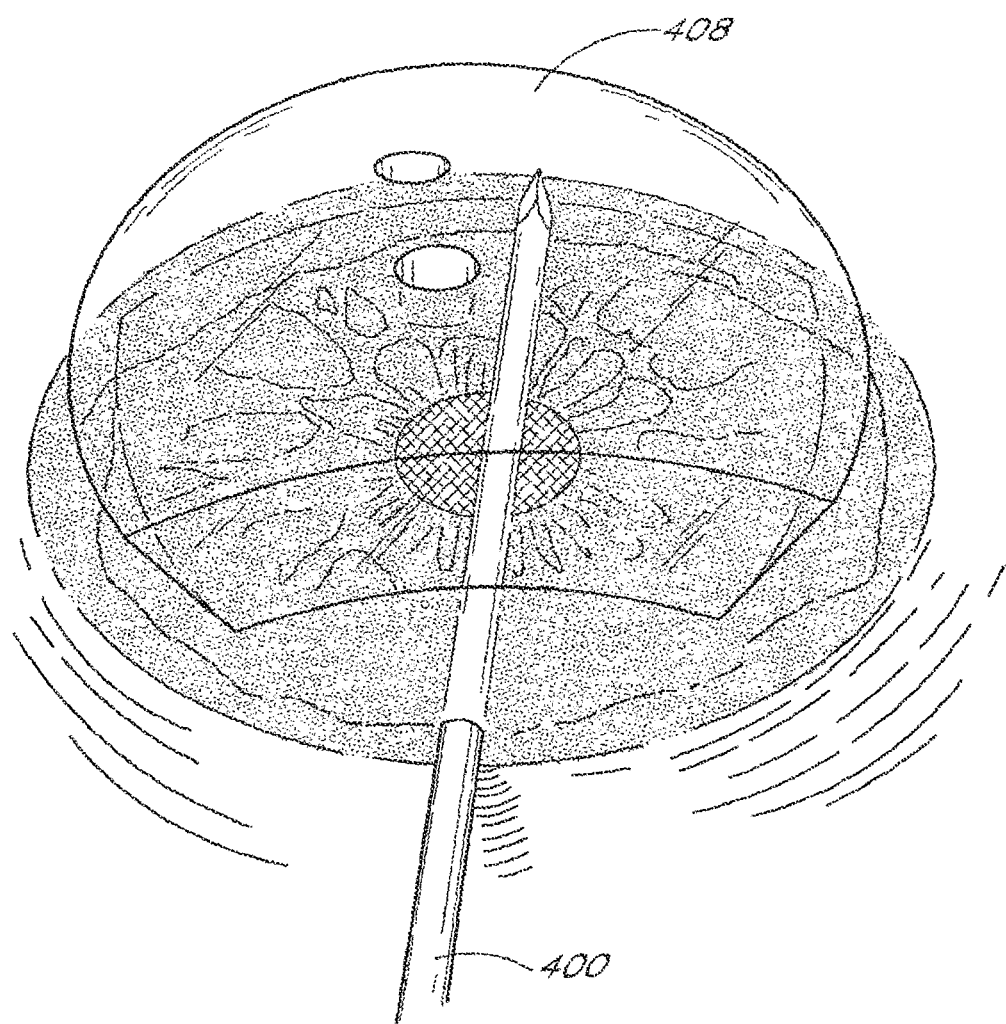

FIGS. 4a-c show the steps for performing a goniotomy procedure. As shown in FIG. 4a, locking forceps 406 are typically used to grasp the inferior and superior rectus muscles. A goniotomy lens 408 is positioned on the eye. A goniotomy knife 400 is inserted from the temporal aspect beneath the goniotomy lens and viewed through a microscope. The cornea is irrigated with balanced salt solution. The surgeon positions the goniotomy lens 408 on the cornea, holding the lens 408 with an angled, toothed forceps 406 placed into the two dimples at the top of the lens 408.

The surgeon places the goniotomy knife 400 into and through the cornea 1.0 mm anterior to the limbus, maintaining the knife 400 parallel to the plane of the iris (FIG. 4b). Slight rotation of the knife 400 facilitates smooth penetration into the anterior chamber without a sudden break through the cornea. The surgeon continues to gently apply pressure and rotate the goniotomy knife 400, directing it across the chamber, parallel to the plane of the iris, until reaching the trabecular meshwork in the opposite angle.

The surgeon visualizes the trabecular meshwork under direct microscopy and engages the superficial layers of the meshwork at the midpoint of the trabecular band. The incision is typically made 100° to 120°, as designated by a in FIG. 4b, circumferentially, first incising clockwise 50° to 60°, then counterclockwise for 50° to 60°.

As the tissue is incised, a white line can be seen and the iris usually drops posteriorly. An assistant facilitates incision by rotating the eye in the opposite direction of the action of the blade (FIG. 4c).

The surgeon completes the goniotomy incision and promptly withdraws the blade. If aqueous escapes from the wound and the chamber is shallow, the surgeon can slide the goniotomy lens over the incision as the blade is withdrawn. The anterior chamber can be reformed with an injection of balanced salt solution through the external edge of the corneal incision. The leak can be stopped using a suture and burying the knot.

Trabeculodialysis.

Figure 5A:
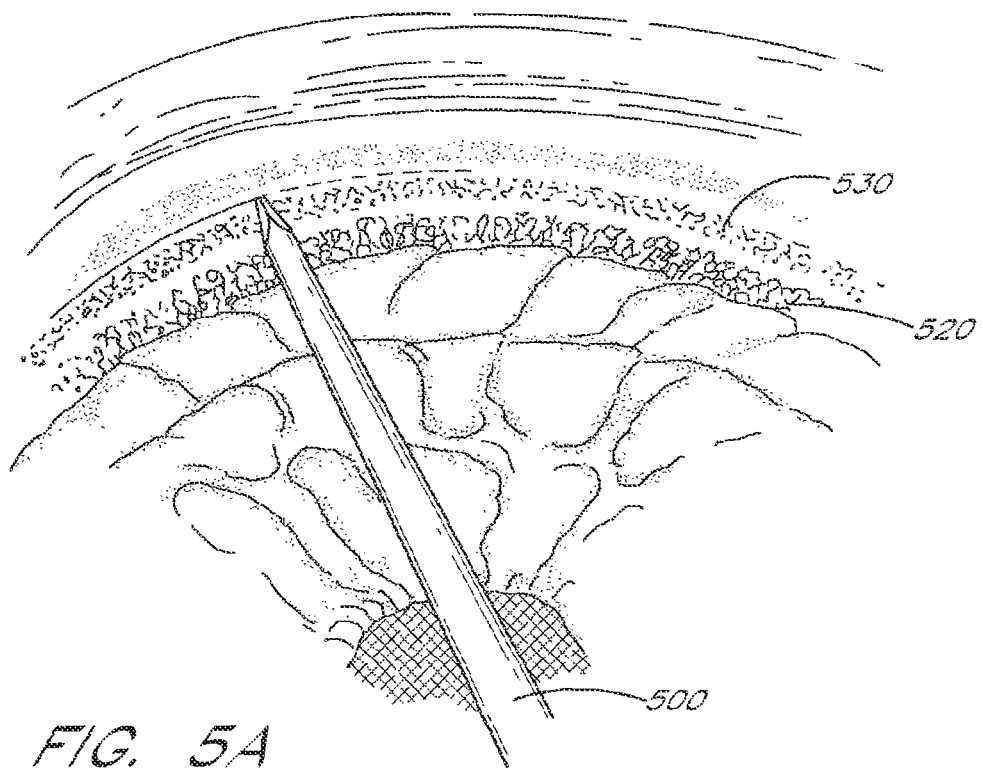
FIGS. 5a-d show diagrammatically the steps of performing a trabeculodialysis.

Trabeculodialysis is similar to goniotomy but is performed primarily in young patients with glaucoma secondary to inflammation. Trabeculodialysis differs from goniotomy only in the position of the incision. FIGS. 5a-d show the steps of a trabeculodialysis procedure. The knife 500 passes across the anterior chamber and engages the trabecular meshwork at Schwalbe's line rather than at the midline of the meshwork, as shown in FIG. 5a.

Figure 5B:
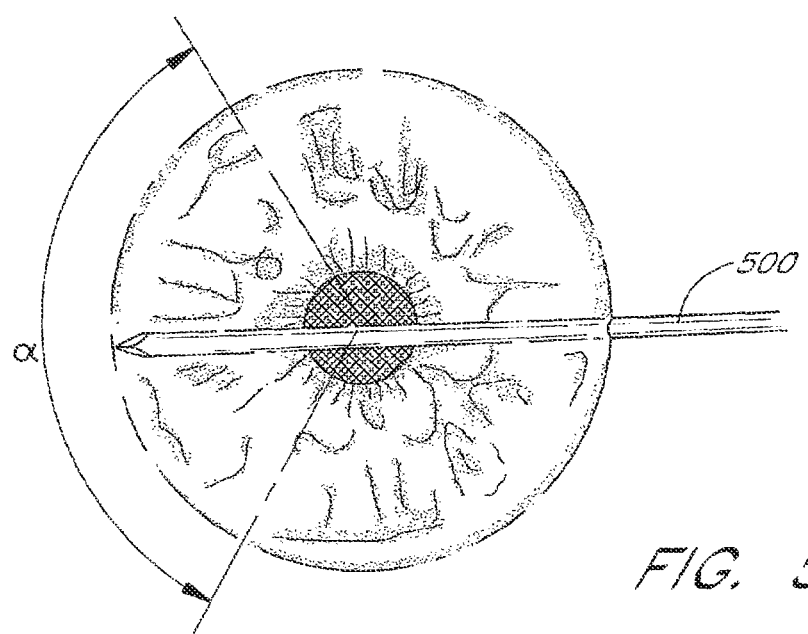

The incision is typically made 100° to 120° circumferentially, as designated by a in FIG. 5b, first incising clockwise 50° to 60°, then counterclockwise for 50° to 60° (FIG. 5b).

Figure 5C:
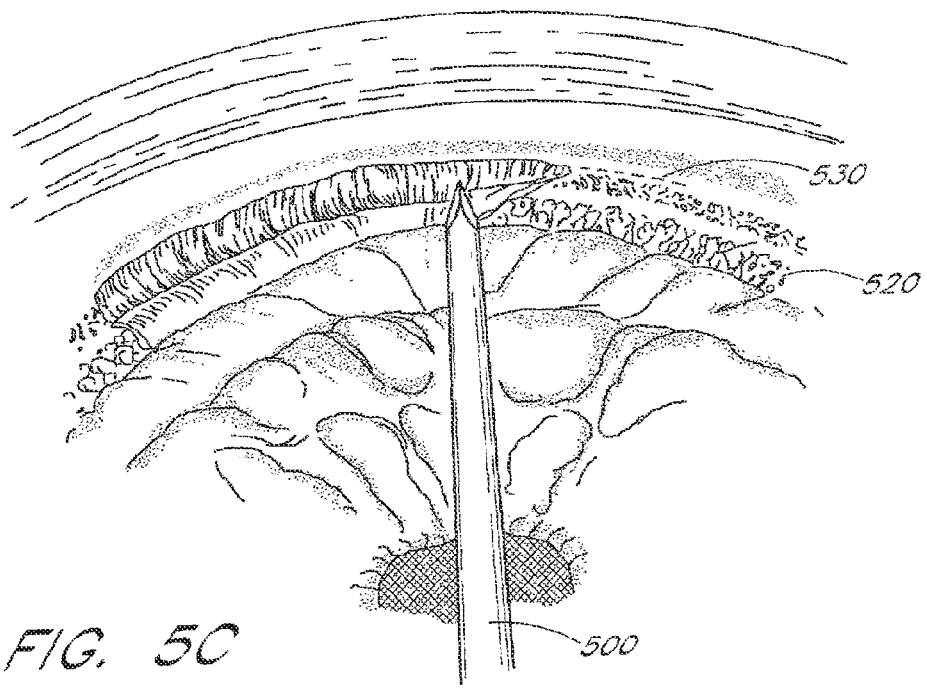
Figure 5D:
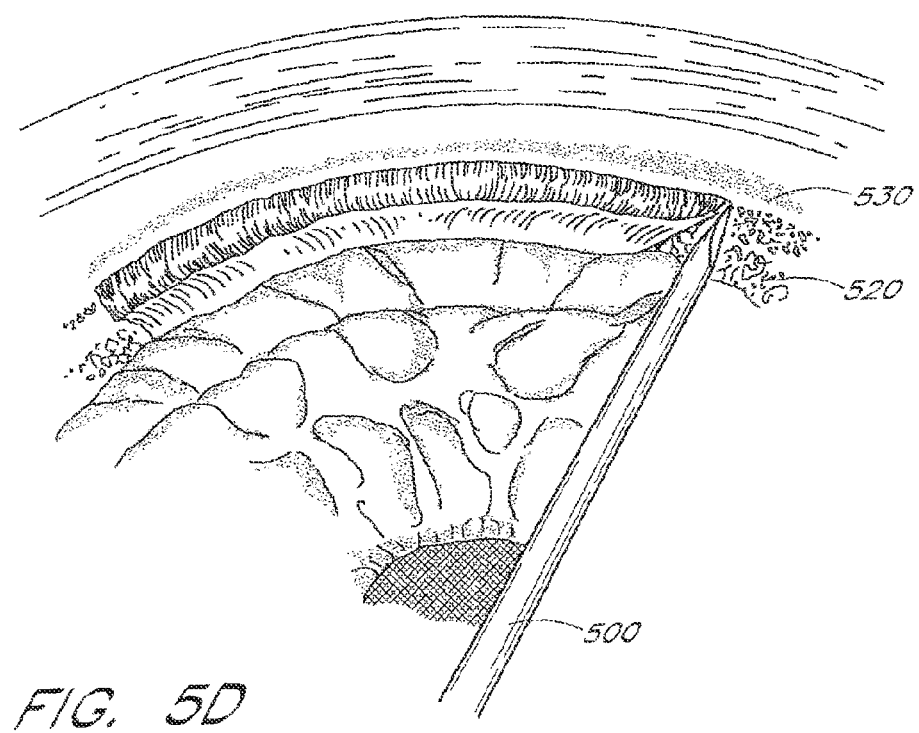
Figure 6A:
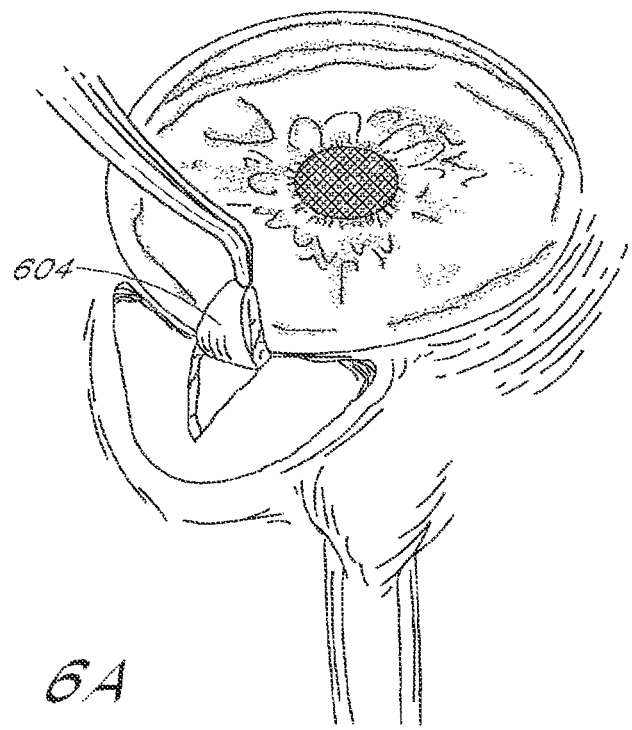
FIGS. 6a-f show diagrammatically the steps of a trabeculotomy procedure using a probe of a preferred embodiment.
Figure 6B:
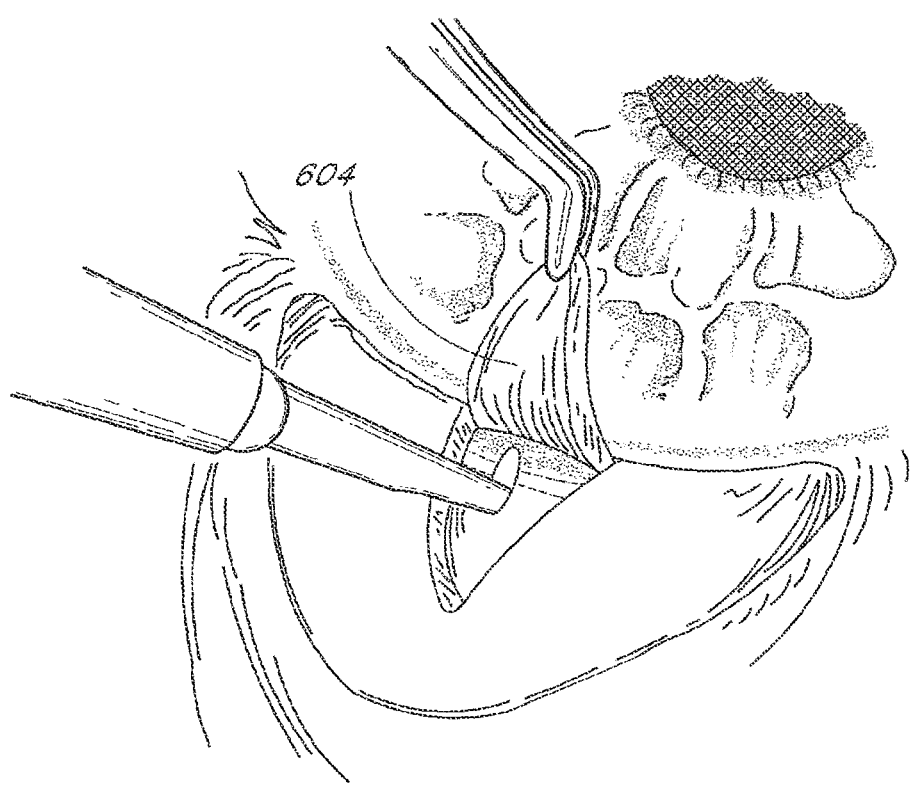
Figure 6C:
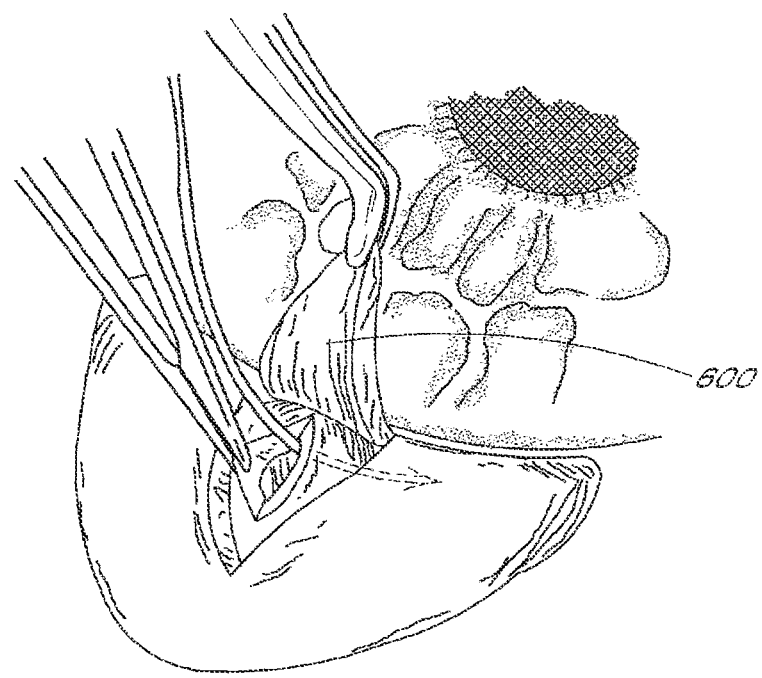
Figure 6D:
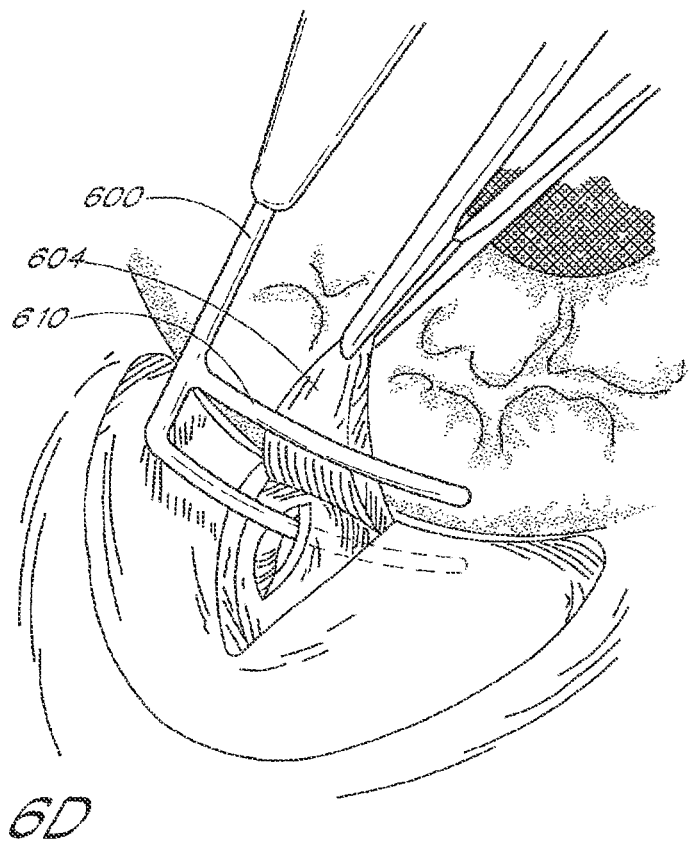

With the flat side of the blade, the surgeon pushes the trabecular meshwork inferiorly toward the surface of the iris, as shown in FIG. 5c. FIG. 6d shows the meshwork, disinserted from the scleral sulcus, exposing the outer wall of Schlemm's canal.

Trabeculotomy.

Trabeculotomy displaces trabecular meshwork as a barrier to aqueous outflow. Initially, the surgeon creates a triangular scleral flap 604 that is dissected anteriorly of the limbus, as shown in FIG. 6a. A radial incision is made over the anticipated site of Schlemm's canal (FIG. 6b). The incision is deepened until the roof of Schlemm's canal is opened (FIG. 6c).

The surgeon locates Schlemm's canal through the external surface of the limbus, threads a trabeculotome 600 into the canal and rotates the instrument into the anterior chamber, as shown in FIG. 6d. The upper arm 610 of the instrument should be kept parallel to the plane of the iris. The instrument 600 is then rotated within the anterior chamber and maintained parallel to the iris. After rotating the instrument 600 through the meshwork in one direction, the surgeon withdraws the instrument and inserts a second instrument with the opposite curve. The identical procedure is then performed in the opposite direction.

Figure 6E:
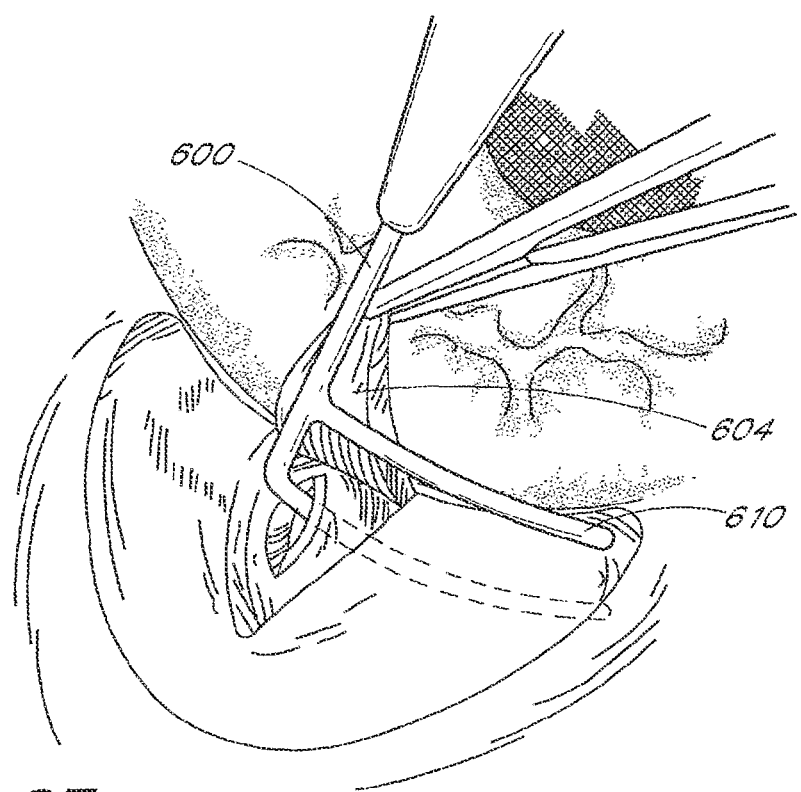
Figure 6F:
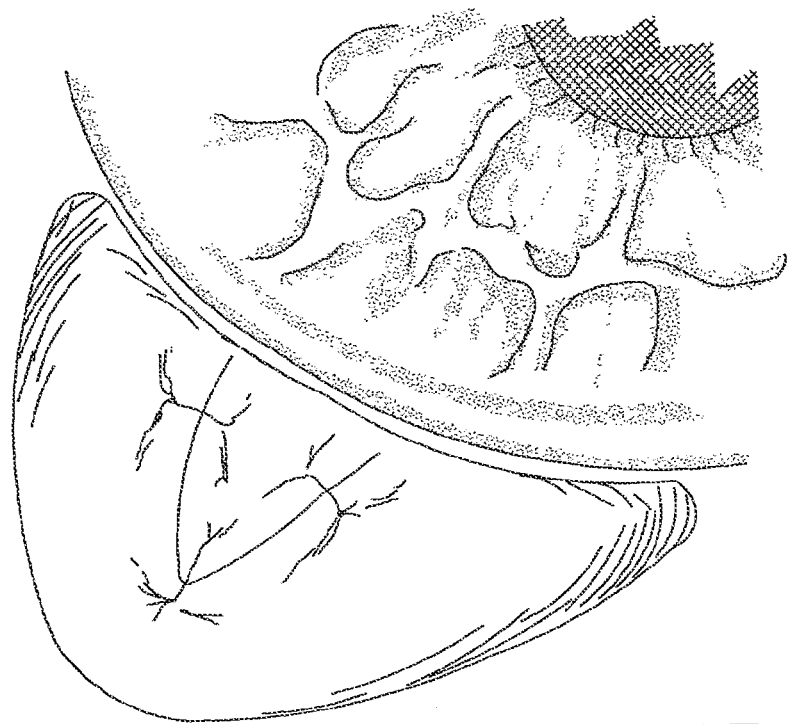

Collapse of the anterior chamber often occurs during the procedure. The chamber can be reformed by injecting irrigation fluid. Aspiration may be used to remove the tissue. The scleral flap 604 may then be sutured closed, as shown in FIG. 6e.

Goniectomy Cauterization Probe.

Figure 7:
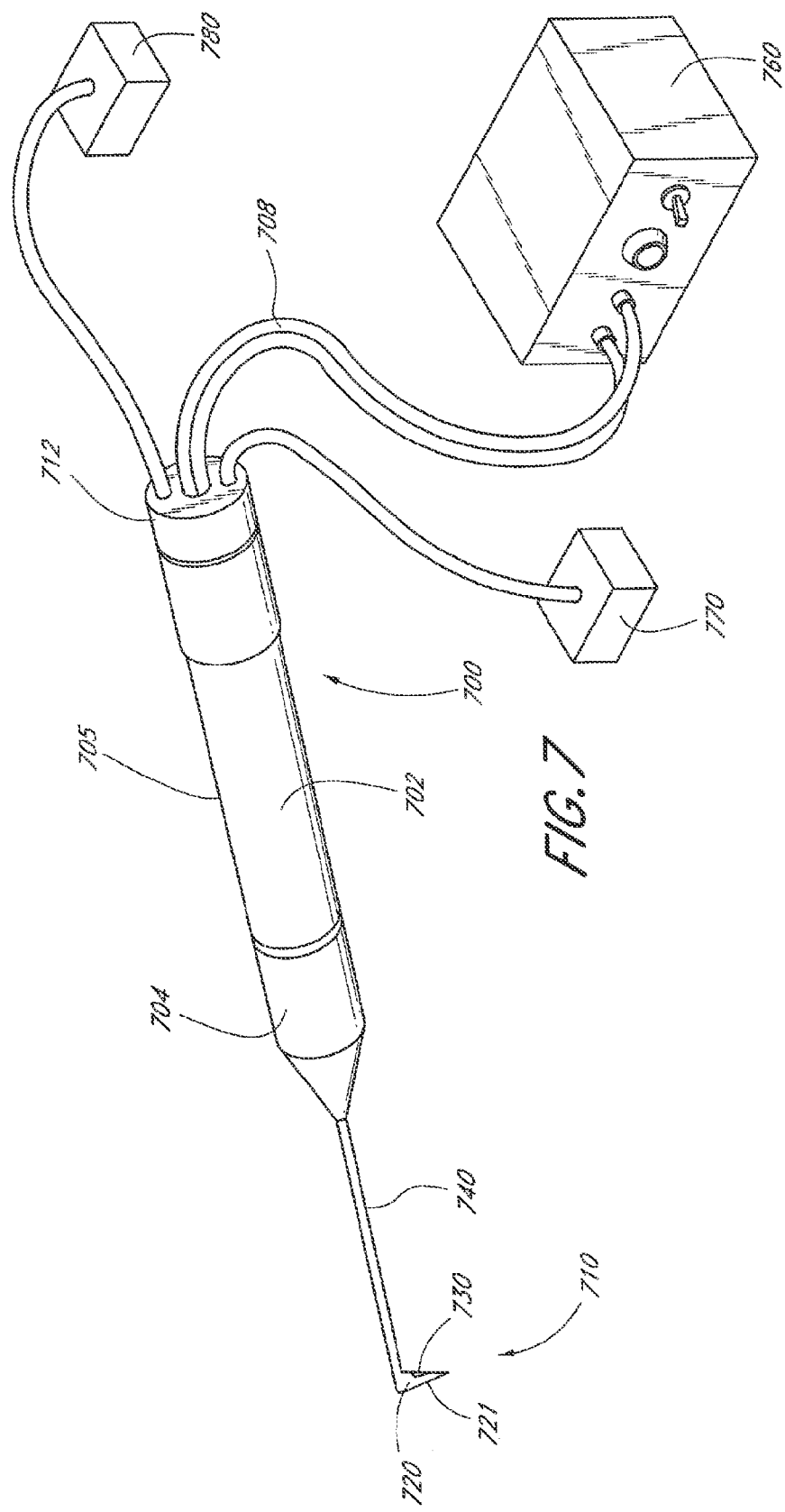
FIG. 7 is a perspective view which shows a goniectomy cautery probe of a preferred embodiment.
Figure 8:
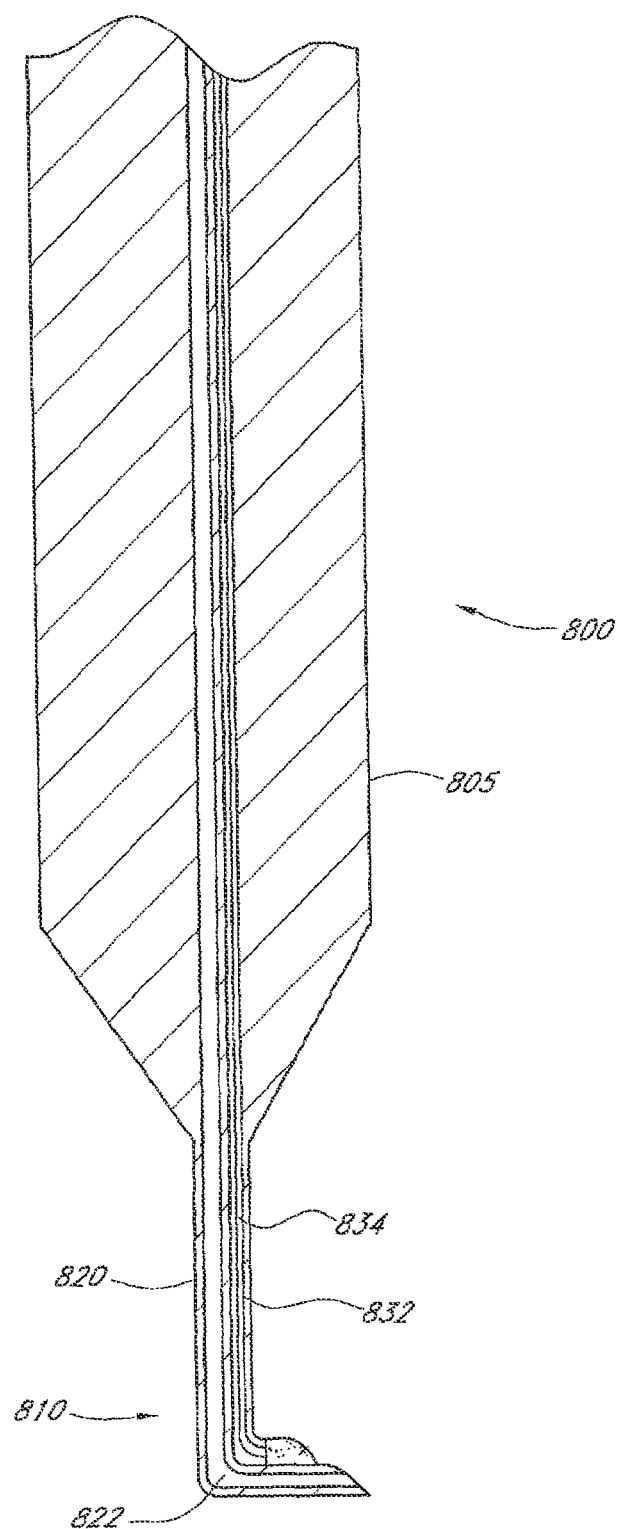
FIG. 8 is a cross-sectional schematic diagram which shows the goniectomy cautery probe of FIG. 7.

A preferred embodiment of a goniectomy probe, used to cauterize and ablate the trabecular meshwork is shown in FIGS. 7 and 8. The probe 700 comprises a handle 705 and a probe tip 710. Preferably, the handle is approximately 20 gauge and the probe tip is approximately 27 gauge. The proximal end of the handle is adapted for mating with a connector 712 to the output terminals of an energy source 760.

The probe also includes electrical leads 834 (FIG. 8), a power cable 708, preferably a coaxial cable, and actuation means. These components extend from the handle 705, through an electrical lead lumen 832 (FIG. 8) in the probe shaft 705, to the corresponding components of the probe 700 disposed on the distal end. The proximal ends of the cables and lumens connect to the corresponding connectors that extend from the distal end of the probe handle 705.

Figure 9:
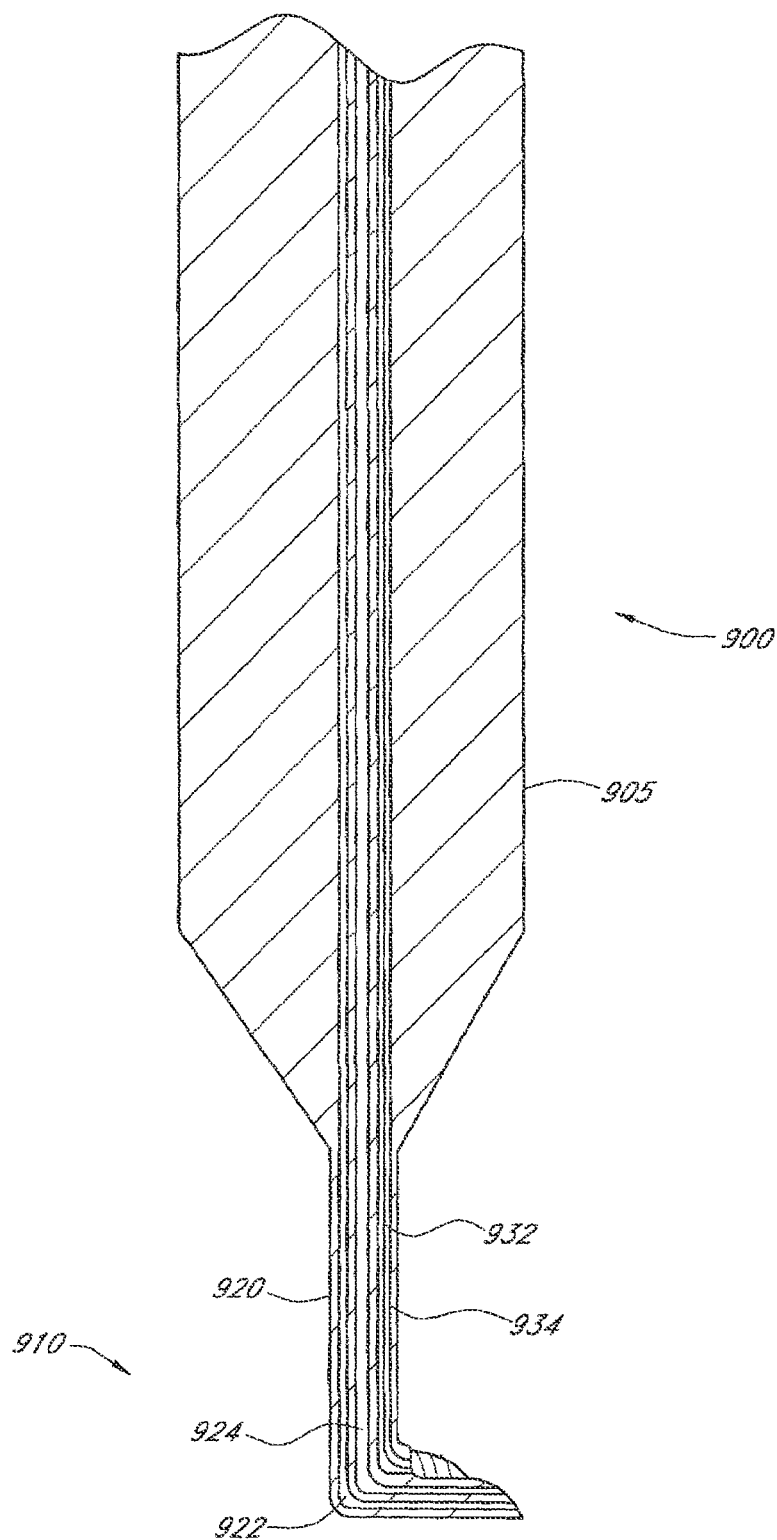
FIG. 9 is a cross sectional schematic diagram which shows another embodiment of the goniectomy cautery probe of FIG. 7.

Aspiration and irrigation may be provided by an aspiration pump 770 and irrigation pump 780. The aspiration pump 770 is connected to a standard vacuum supply line to promote the withdrawal of the aspiration fluid. Aspiration vacuum control may be provided by an aspiration valve. In a preferred embodiment, as shown in FIG. 8, both irrigation and aspiration may be provided by the same lumen 822, alternating the pump as needed. However, the irrigation lumen 922 and aspiration lumen 924 are separate in the embodiment of FIG. 9, providing for simultaneous irrigation and aspiration. Irrigation under pressure flushes blood from the eye and expands the anterior chamber, providing more room for the procedure.

The handle 705 may be made of an electrically insulating polymeric material, configured in a pencil-shape form having a cylindrical body region 702 and a tapered forward region 704. A contoured handle helps to reduce the holding force required and increase proprioceptive sensitivity. Although a pencil-shape configuration is preferred, it is noted that any configuration of the handle 705 which is easily, comfortably and conveniently grasped by the operator will also be suitable and is considered to be within the scope of the present invention.

The probe tip 710 is connected to the main body of the handle 705. The probe tip further comprises a footplate 721, which protects the collector channels, penetrates the trabecular meshwork, and serves as a guide in Schlemm's canal. The cautery element 730, located at the distal end of the probe tip 710 may have a variety of configurations.

The tip 710 may be any material, such as titanium, brass, nickel, aluminum, stainless steel, other types of steels, or alloys. Alternatively, non-metallic substances may also be used, such as certain plastics. The malleable probe tips can be configured as straight, angled or curved, for example, which provides for optimal access to specific anatomy and pathology. Unique tip designs improve tactile feedback for optimal control and access, and provide for improved tissue visualization with greatly reduced bubbling or charring.

The probe tip 710 comprises an electrode 730, suitable for cautery, as known to those of skill in the art. Various electrode configurations and shapes may be suitable. The cautery element 730 may be any electrode that may provide ablation or cauterization of tissue, such as an ultrasound transducer, a RF electrode, or any other suitable electrode.

The cautery element may also include other cautery energy sources or sinks, and particularly may include a thermal conductor. Examples of suitable thermal conductor arrangements include a metallic element which may, for example, be constructed as previously described. However, in the thermal conductor embodiment such a metallic element would be generally resistively heated in a closed loop circuit internal to the probe, or conductively heated by a heat source coupled to the thermal conductor.

The probe tip may have a coating such as a non-stick plastic or a coating comprising diamond to prevent undesirable sticking or charring of tissue. The electrode may be provided on the inner surface of the tip. Alternatively, the electrode is embedded in a sheath of a tube. Insulation is provided around the cautery element so that other areas of the eye are not affected by the cauterization. A sleeve shield or a non-conductive layer may be provided on the probe tip to expose only a selected portion of the electrode. The sleeve preferably has sufficient thickness to prevent both current flow and capacitance coupling with the tissue.

The electrode or other device used to deliver energy can be made of a number of different materials including, but not limited to stainless steel, platinum, other noble metals, and the like. The electrode can also be made of a memory metal, such as nickel titanium. The electrode can also be made of composite construction, whereby different sections are constructed from different materials.

In a preferred embodiment, the probe assembly is bipolar. In a bipolar system, two electrodes of reversed polarity are located on the probe tip, thus eliminating the contact plate for completion of the circuit. Additionally, any number of pairs of electrodes may be provided on the probe tip.

In an alternative embodiment, the probe assembly is monopolar. In a monopolar system, the system comprises a single electrode and a contact plate is attached to the surface of the human body. The contact plate is further connected to the minus terminal of the power source via a lead wire. Voltages of reversed polarity are applied to the electrode and the contact plate.

Figure 10B:
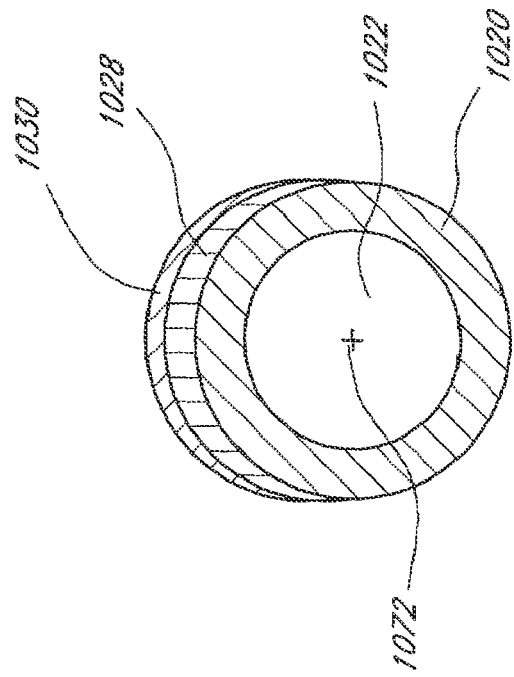
FIG. 10b is a cross-sectional schematic diagram which shows the probe tip of the goniectomy cautery probe of FIG. 7.
Figure 10A:
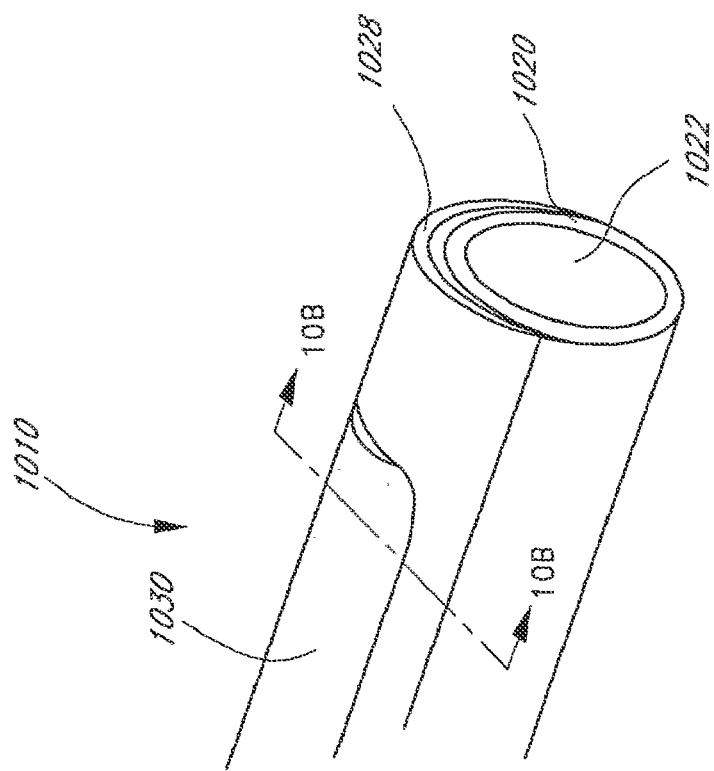
FIG. 10a is a detailed view which shows the probe tip of the goniectomy cautery probe of FIG. 7.

In a preferred embodiment as shown in FIGS. 10a and 10b, an electrode assembly of a bipolar probe includes one electrode 1020 made from a stainless steel 20 gauge hollow needle and a second electrode 1030 formed as a layer of electrically conductive material (such as silver or nickel) deposited over and adhered on an exterior surface of the needle electrode 1020. A thin electrical insulator 1028 separates the electrodes 1020, 1030, along their lengths to avoid short circuiting.

The electrode 1020 extends along a longitudinal axis 1072 of the footplate 721 (FIG. 7) from a proximal region at which bipolar electrical power is applied to a distal region of the electrode assembly.

In a preferred embodiment, the second electrode 1030 extends over a limited portion of the circumference of the first electrode 1020, rather than entirely around the first electrode. Current flows over a relatively small portion of the circumference and length of the first electrode 1020. This limits the area in the body that receives current, and provides the operator with a high degree of control as to where the current is applied. The second electrode 1030 extends over an arc of approximately one quarter of the circumference of the first electrode 1020. The second electrode 1030 is disposed symmetrically about an axis 1072.

In a preferred embodiment, the first electrode, and thus the footplate 721, has a central passage 1022 that is open at the distal region, providing for irrigation and aspiration. The irrigation and aspiration lumens extend from the distal end of the probe tip 1010, through the probe handle, to the connector, providing for irrigation and aspiration capability.

Figure 11B:
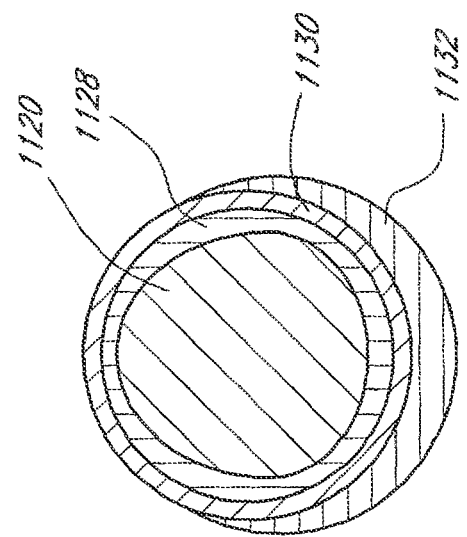
FIG. 11b is a cross-sectional schematic diagram which shows the probe tip of the goniectomy cautery probe of FIG. 7.
Figure 11A:
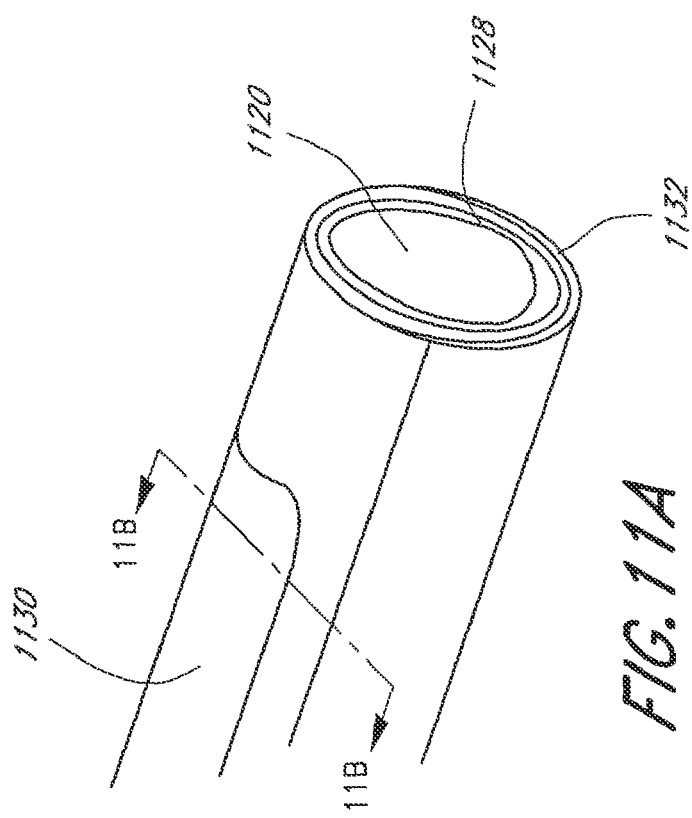
FIG. 11a is a detailed view which shows the probe tip of the goniectomy cautery probe of FIG. 7.

In an embodiment as shown in FIGS. 11a and 11b, the electrode assembly includes a central or axial electrode 1120 formed by a solid cylindrical metal member, and an elongate hollow outer electrode 1130 formed by a cylindrical metal tube member, which is coaxially positioned around the central electrode 1120. The cylindrical outer surface of electrode 1130 forms the circumferential surface of the probe. The outer electrode 1130 is preferably made of stainless steel or other corrosive resistant, conductive material for strength as well as conductivity. The inner electrode 1120 may be made of copper, but less conductive materials may also be employed. The coaxial relationship and spacing between the electrodes 1120, 1130, as well as their electrical isolation from one another, is provided by a tubular sleeve 1128 of an electrically insulating material between the electrode.

A layer of insulation 1132 may also surround the second electrode 1130. One or more regions of insulating area 1132 may be removed at any suitable location along the axis to expose a region of electrode 1130. Cauterization would occur at the exposed region. The circumferential extent of the second electrode 1130 can be further limited, depending on the degree of control desired over the size of the area to which current is applied.

Figure 12B:
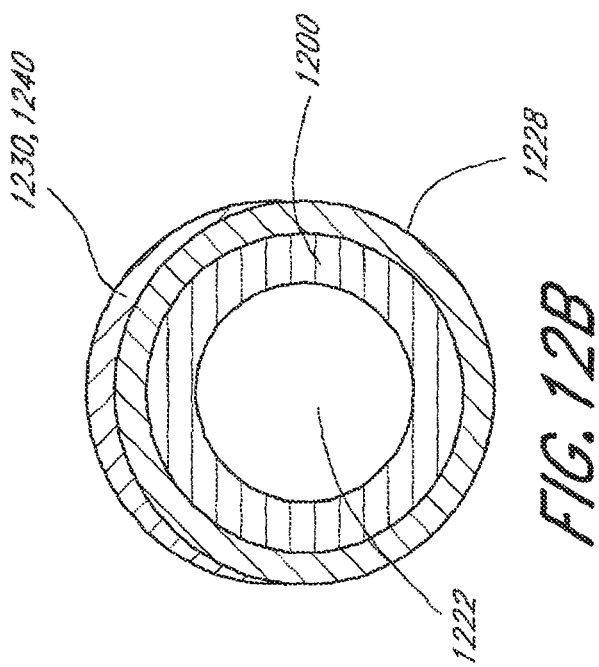
FIG. 12b is a cross-sectional schematic diagram which shows the probe tip of the goniectomy cautery probe of FIG. 7.
Figure 12A:
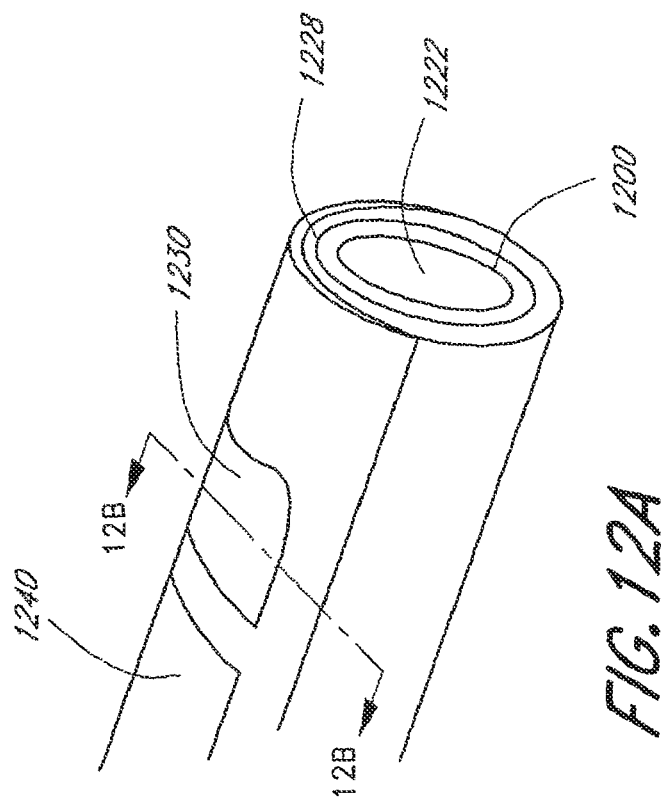
FIG. 12a is a detailed view which shows the probe tip of the goniectomy cautery probe of FIG. 7.

In an alternative embodiment, as shown in FIG. 12, the active region at a remote end of a bipolar electrode is formed by a hollow metal tube 1200 having a substantially cylindrical layer of insulation 1228 on the outer surface of the metal tube. The metallic tube 1200 is not an electrode and is provided only for the strength of the probe assembly. The tip supports two metal electrodes 1230, 1240. Each of the electrodes 1230, 1240 have electric leads, which extend through the hollow interior of the tube 1200 to a supporting insulative handle where it is coupled by appropriate means with a power source in the manner previously described. Energy flows between the electrodes 1230, 1240, heating only the tissue adjacent the gap therebetween. Aspiration and irrigation may be provided through a lumen 1222.

Figure 13:
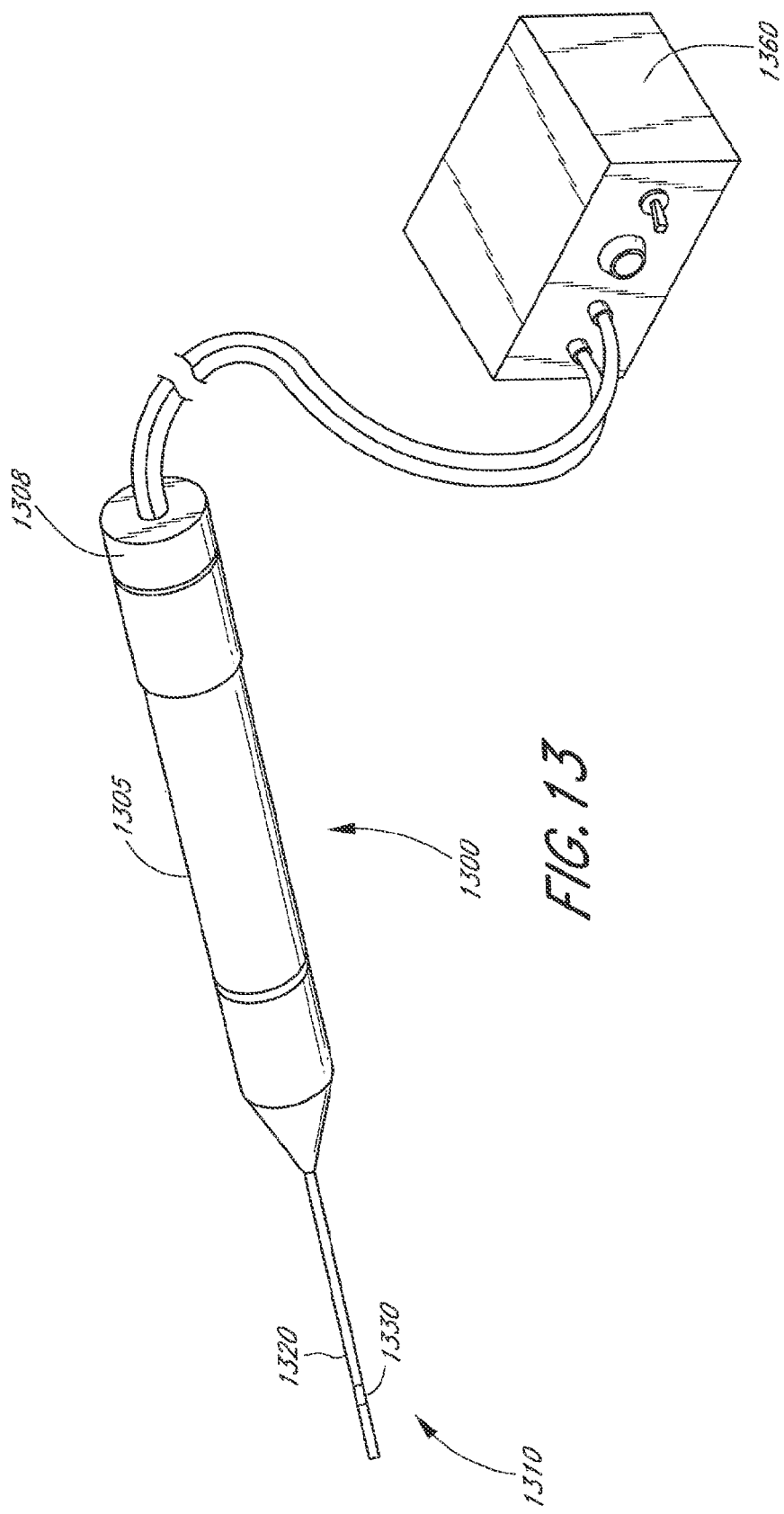
FIG. 13 is a perspective view which shows a goniectomy cautery probe of a preferred embodiment.
Figure 14:
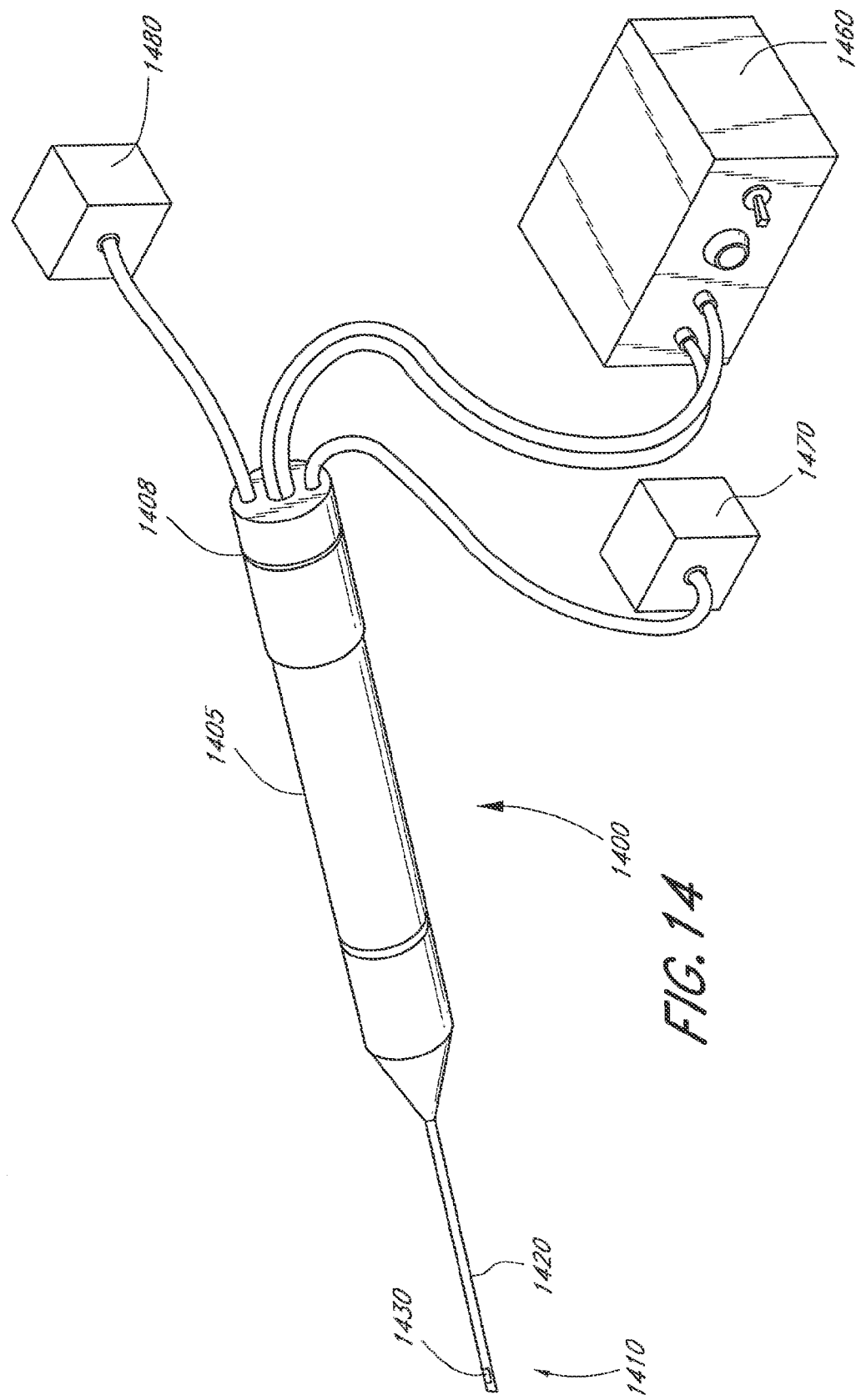
FIG. 14 is a perspective view which shows a goniectomy cautery probe of a preferred embodiment.

FIGS. 13 and 14 show alternative embodiments of a goniectomy cauterization probe 1300, 1400. The probe comprises a handle 1305, 1405 and a probe tip 1310, 1410. The probe tip includes a cautery element 1330, 1430.

The probes 1300, 1400 are provided with an energy source; however, probe 1400 also includes an irrigation supply 1480 and an aspiration pump 1470. These components connect to the probe 1300, 1400 at connector 1308, 1408.

FIGS. 15 a,b show detailed views of probe tip 1310. The probe tip 1510 is straight and includes an electrode 1530 attached to electrode 1520, which are separated by a layer of insulation 1528.

FIGS. 16 a,b show detailed views of probe tip 1410. The probe tip 1610 is straight and includes an electrode 1630 attached to a hollow electrode 1620, which are separated by a layer of insulation 1628. The hollow electrode 1620 forms a hollow passage 1622 for irrigation and aspiration.

In an alternative embodiment, the needle tip of FIG. 14 may comprise a hollow needle, with or without a cauterizing element, acoustically coupled to an ultrasonic handle and surrounded by a hollow sleeve. The handle includes an ultrasonic transducer, such as that used for phacoemulsification, which may be either piezoelectric or magnetostrictive. When the handle is activated, the needle is vibrated longitudinally at an ultrasonic rate. Simultaneously, a hydrodynamic flow of irrigation fluid may be introduced into the eye. The vibrating needle emulsifies the tissue, and the particles are preferably simultaneously aspirated, along with the fluid, out of the eye through the hollow needle tip. Aspiration is effected by a vacuum pump, which is connected to the handle. The ultrasonically vibrated needle emulsifies the tissue by combining i) the mechanical impact of the needle tip which varies depending on its mass, sharpness, and acceleration, ii) the ultrasonic acoustical waves generated by the metal surfaces of the vibrating needle, iii) the fluid wave created at the needle's leading edge, and iv) implosion of cavitation bubbles created at the tip of the vibrating needle.

In an alternative embodiment, sonic technology may be used to ablate the tissue. Sonic technology offers an innovative means of removing material without the generation of heat or cavitational energy by using sonic rather than ultrasonic technology. The tip expands and contracts, generating heat, due to intermolecular frictional forces at the tip, that can be conducted to the surrounding tissues. The tip does not need a hollow sleeve if sonic energy is used to remove the trabecular meshwork.

The use of acoustic energy, and particularly ultrasonic energy, offers the advantage of simultaneously applying a dose of energy sufficient to ablate the area without exposing the eye to current. The ultrasonic driver can also modulate the driving frequencies and/or vary power in order to smooth or unify the produced collimated ultrasonic beam.

The amount of heat generated is directly proportional to the operating frequency. The sonic tip does not generate cavitational effects and thus true fragmentation, rather than emulsification or vaporization, of the tissue takes place. This adds more precision and predictability in cutting and less likelihood of damage to other areas of the eye. The tip can be utilized for both sonic and ultrasonic modes. The surgeon can alternate between the two modes using a toggle switch on a foot pedal when more or less energy is required.

FIG. 17 shows the control system for a goniectomy cauterization probe. The cautery element 1730 is coupled to a cautery actuator. The cautery actuator generally includes a radiofrequency ("RF") current source 1760 that is coupled to both the RF electrode and also a ground patch 1750 which is in skin contact with the patient to complete an RF circuit, in the case of a monopolar system. The cautery actuator may include a monitoring circuit 1744 and a control circuit 1746 which together use either the electrical parameters of the RF circuit or tissue parameters such as temperature in a feedback control loop to drive current through the electrode element during cauterization. Also, where a plurality of cautery elements or electrodes are used, switching capability may be provided to multiplex the RF current source between the various elements or electrodes.

The probe is connected to a low voltage power source via a power cord that mates with the handle. The source may be a high frequency, bipolar power supply, preferably, a solid state unit having a bipolar output continuously adjustable between minimum and maximum power settings. The source is activated by an on/off switch, which may comprise a foot pedal, or a button on the probe or interface. The source provides a relatively low bipolar output voltage. A low voltage source is preferred to avoid arcing between the electrode tips, which could damage the eye tissue. The generator is coupled to first and second electrodes to apply a biologically safe voltage to the surgical site.

Delivery of energy to the tissue is commenced once the cautery element is positioned at the desired location. The energy source preferably provides RF energy, but is not limited to RF and can include microwave, ultrasonic, coherent and incoherent light thermal transfer and resistance heating or other forms of energy as known to those of skill in the art. Energy is typically delivered to the cautery element via electrical conductor leads. The cautery control system may include a current source for supplying current to the cautery element.

The current source is coupled to the cautery element via a lead set (and to a ground patch in some modes). The monitor circuit 1744 desirably communicates with one or more sensors (e.g., temperature) 1730 which monitor the operation of the cautery element. The control circuit 1746 may be connected to the monitoring circuit 1744 and to the current source 1760 in order to adjust the output level of the current driving the cautery element based upon the sensed condition (e.g. upon the relationship between the monitored temperature and a predetermined temperature set point).

The procedure for performing goniectomy with the goniectomy cauterization probe of an embodiment of the present invention is similar to a traditional goniotomy surgery, as previously described. The surgeon preferably sits on the temporal side of the operating room table utilizing an operating microscope. The patient's head is rotated 45° away from the surgeon after a retrobulbar injection has anesthetized the eye. A knife, preferably 20 gauge, is used to make a clear corneal temporal incision. The goniectomy instrument is inserted into the anterior chamber up to the infusion sleeve to maintain the intraocular pressure and deepen the anterior chamber. The surgeon positions the gonio lens, preferably a Schwann-Jacobs lens or a modified Barkan goniotomy lens, on the cornea. The goniectomy probe is advanced to the trabecular meshwork. The sharp end point of the footplate incises the middle one third of the trabecular meshwork, which is known as the pigmented portion of the trabecular meshwork. The footplate 721 (FIG. 7) is further inserted into Schlemm's canal. The cautery element is activated, preferably by a footplate, which may also be used to activate irrigation and aspiration. The current provided to the cautery element heats the tissue. The instrument is slowly advanced through the trabecular meshwork maintaining the footplate 721 in Schlemm's canal, feeding the pigmented trabecular meshwork into the opening of the instrument where the tissue removal occurs. The instrument is advanced until no further tissue can be removed inferiorly. The tissue may also be aspirated through the probe, thus substantially removing a portion of the trabecular meshwork. The instrument may be rotated in the eye and reintroduced into Schlemm's canal where the initial incision began. The superior portion of the trabecular meshwork is then removed using cautery and aspiration. In a preferred embodiment, a substantial portion, preferably at least half, of the trabecular meshwork is removed. The corneal incision is preferably sealed by injecting a balanced salt solution into the corneal stroma or by placing a suture. The anterior chamber is reformed. A visceolastic substance may be utilized to maintain the anterior chamber with the initial incision and at the end of the surgery.

Trabeculodialysis.

Trabeculodialysis is similar to goniectomy; therefore, a goniectomy cauterization probe may also be used to perform trabeculodialysis. The procedure for performing a trabeculodialysis procedure with a cauterization probe is similar to the trabeculodialysis procedure previously described. However, rather than cutting the tissue with a knife, the tissue is ablated with the probe. Similarly, in a preferred embodiment, a substantial portion, preferably at least half, of the trabecular meshwork is removed.

Goniectomy Cutting Probe.

Figure 18:
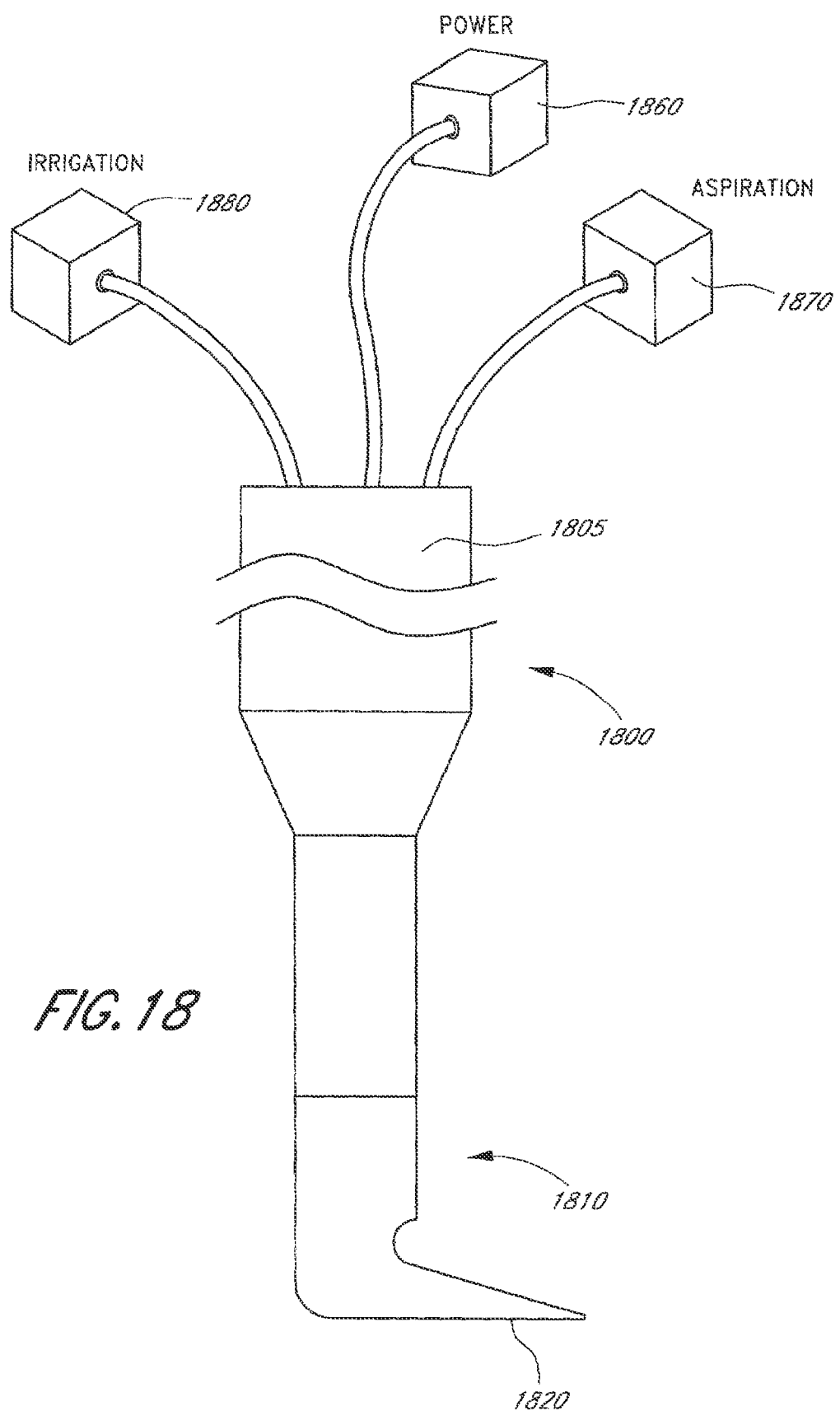
FIG. 18 is a perspective view which shows a goniectomy probe.

Another preferred embodiment of a goniectomy cutting probe, used to cut and remove trabecular meshwork, is shown in FIG. 18. The probe comprises a handle 1805 and a probe tip 1810. Preferably, the handle is 20 gauge and the probe tip is approximately 25 gauge. The handle 2405 is sized and configured to fit completely and comfortably within a hand. The handle 2405 may be formed of a variety of materials, including plastics, and may be designed in a variety of shapes. Generally, it will be preferred that a convenient shape for gripping, such as a cylindrical shape, be provided. The probe tip 1810 further comprises a footplate 1820, protecting endothelial cells and collector channels lining the scleral wall of Schlemm's canal. The footplate 1820 also serves as a guide in Schlemm's canal. The sharpened end of the footplate is used to penetrate the trabecular meshwork.

Figure 19:
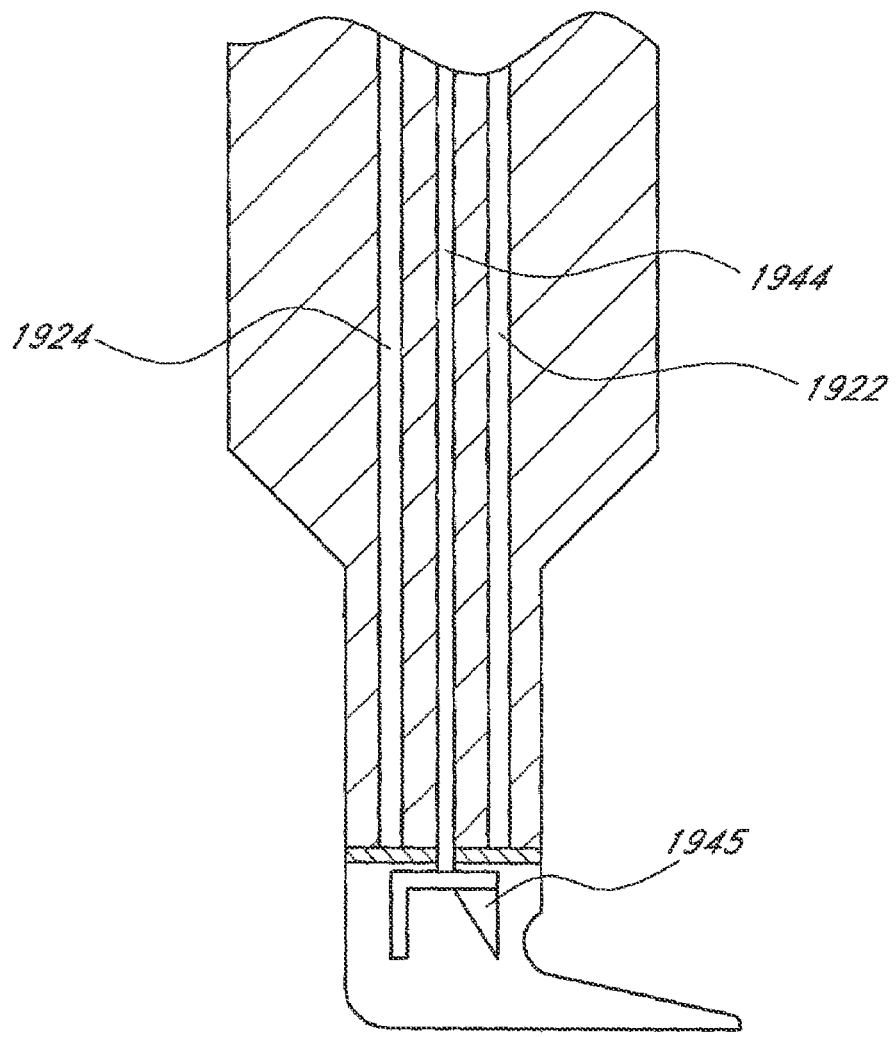
FIG. 19 is a cross-sectional schematic diagram which shows an embodiment of the probe of FIG. 18.
Figure 20:
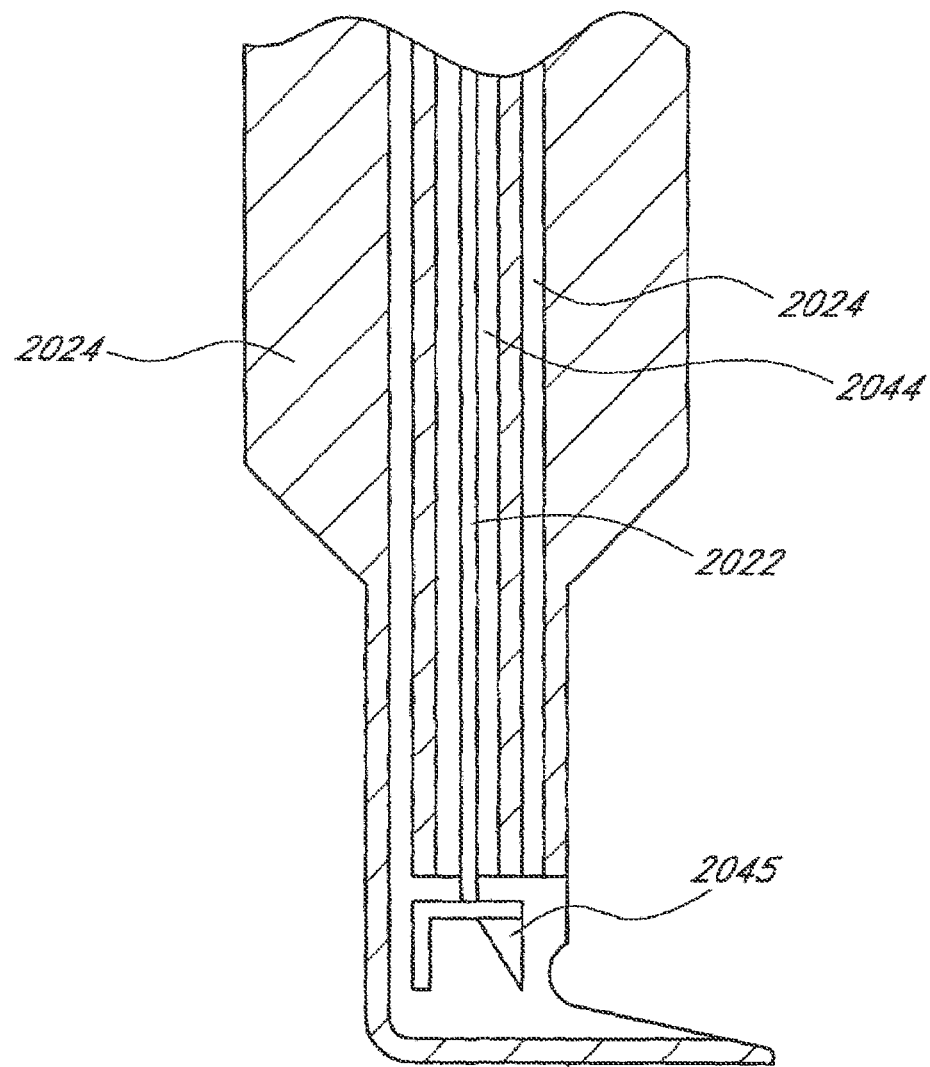
FIG. 20 is a cross-sectional schematic diagram which shows an embodiment of the probe of FIG. 18.

FIGS. 19-20 show sectional views of different embodiments of the internal components and construction of the probe 1800. The probe is configured to define therewithin a hollow inner chamber. A drive member, coupled to a rotatable drive cable within a drive cable assembly, extend into the hollow inner chamber, as shown. A rotatable drive shaft 1944, 2044 is rotatably connected or engaged to the drive member, such that the shaft may be rotatably driven at speeds required for the trabecular meshwork removal. The rotatable drive shaft is inserted into a bore formed in the distal face of the drive member.

The elongate rotatable drive shaft 1944, 2044 passes longitudinally through the probe and terminates, at its distal end, in a cutting head 1945, 2045. A protective tubular sheath may be disposed about the rotatable shaft. The rotatable shaft and/or sheath are axially movable so as to allow the cutting head to be alternately deployed in a) a first non-operative position wherein the cutting head is fully located within the inner bore of the tubular sheath so as to be shielded during insertion and retraction of the instrument or b) a second operative position wherein the cutting head is advanced out of the distal end of the sheath so as to contact and remove the trabecular meshwork. The cutting head 1945, 2045 may be configured such that rotation of the head will create and sustain a forced circulation of fluid within the meshwork. Such forced circulation causes the trabecular meshwork to be pulled or drawn into contact with the rotating. cutting head, without the need for significant axial movement or manipulation of the probe while the cutting head is rotating.

A control pedal may be connected to the motor-drive system to induce actuation/deactuation, and speed control of the rotatable drive cable within the drive cable assembly by the operator. Additional switches or control pedals may be provided for triggering and actuating irrigation and/or aspiration of fluid and/or debris through the probe.

The probe of FIG. 19, shows the probe 1900 having two separate lumens, 1922, 1924, for irrigation and aspiration. The hollow passageway 2022 extending longitudinally through the probe of FIG. 20, containing the rotatable drive shaft, is in fluid communication with an irrigation pump (not shown). By such arrangement, a flow of irrigation fluid may be infused through the tube. A separate lumen 2024 is also provided for aspiration.

The independent processes of irrigation and aspiration may be performed simultaneously with the rotation of the head or while the head is in a non-rotating, stationary mode. It will also be appreciated that the infusion and aspiration pathways may be reversed or interchanged by alternately connecting the aspiration pump to the irrigation tubing and irrigation pump to the aspiration tubing.

Figure 21:
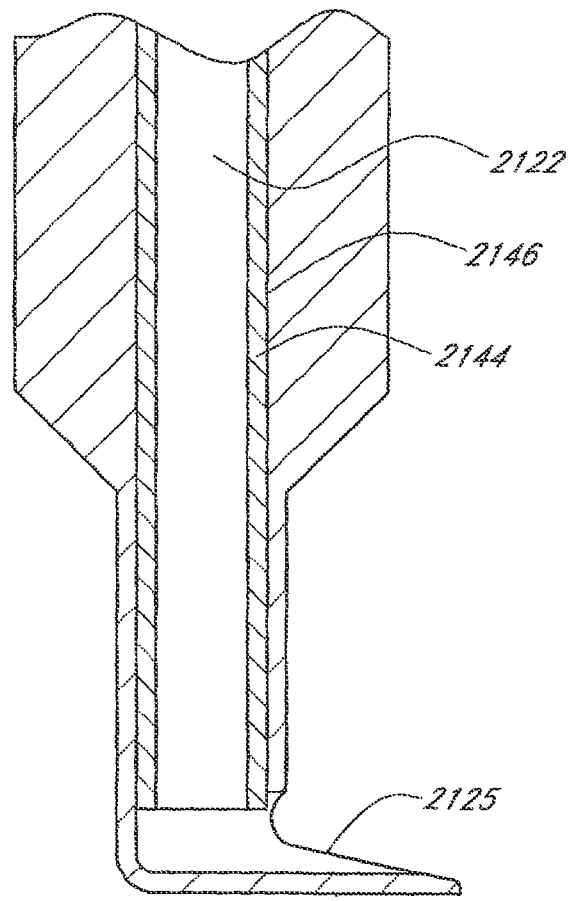
FIG. 21 is a cross-sectional schematic diagram which shows an embodiment of the probe of FIG. 18.
Figure 22:
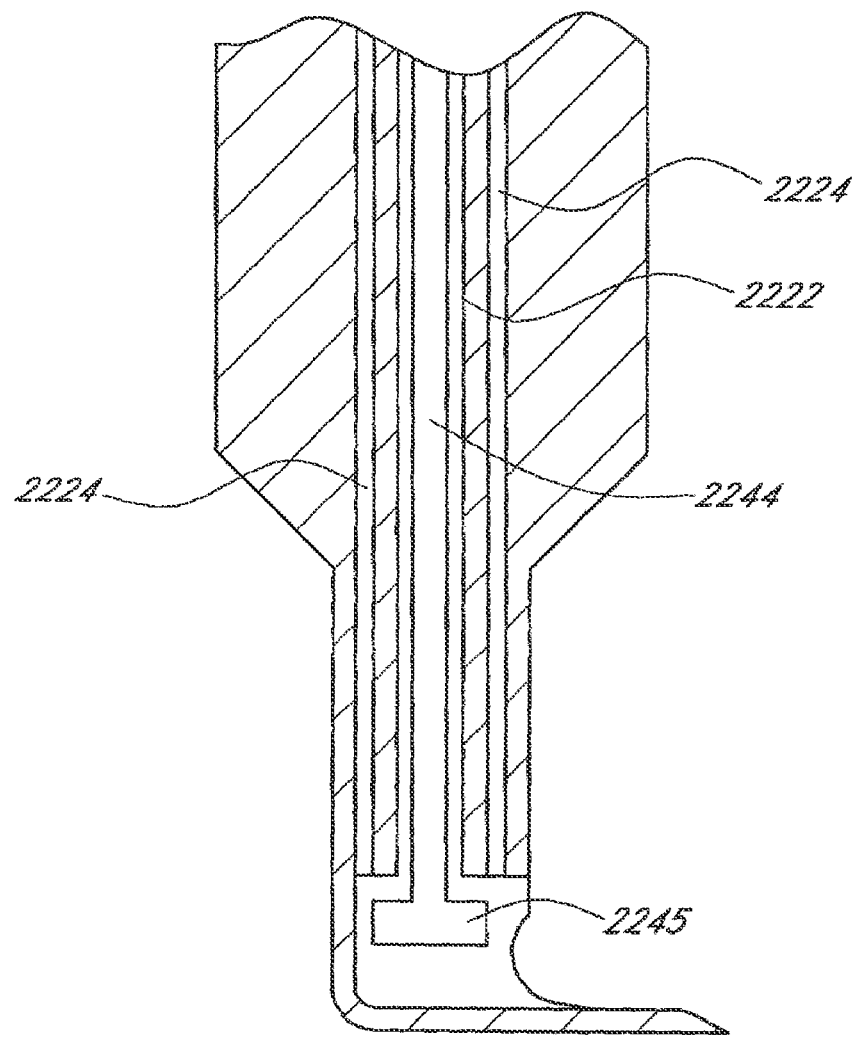
FIG. 22 is a cross-sectional schematic diagram which shows an embodiment of the probe of FIG. 18.
Figure 23:
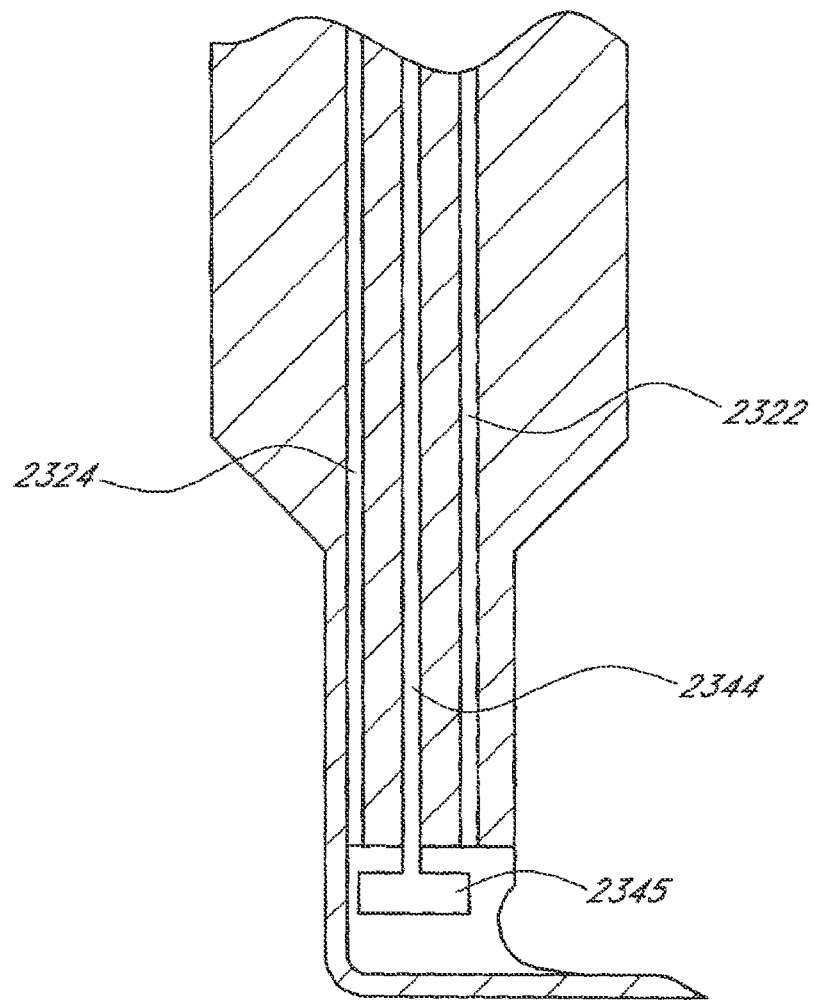
FIG. 23 is a cross-sectional schematic diagram which shows an embodiment of the probe of FIG. 18.

In an alternative embodiment, as shown in FIGS. 21-23, the probe cuts tissue in a guillotine fashion. As shown in FIG. 21, the probe 2100 may include an inner sleeve 2144 that moves relative to an outer sleeve 2146. The sleeves are coupled to the handle. The inner sleeve 2144 may be coupled to a vacuum system which pulls tissue into the port 2125 when the inner sleeve 2144 moves away from the port. The inner sleeve 2144 then moves in a reverse direction past the outer port to sever tissue in a guillotine fashion. The vacuum system draws the severed tissue away from the port, so the process may be repeated. The inner sleeve may be connected to a diaphragm and a spring, rigidly attached to the handle. The diaphragm is adjacent to a pneumatic drive chamber that is in fluid communication with a source of pressurized air (not shown). The drive chamber is pressurized, expanding the diaphragm. Expansion of the diaphragm moves the inner sleeve so that the tissue within the port is severed by the sleeve. Alternatively, the inner sleeve 2144 is driven by a motor located within the handle. The inner sleeve 2144 is coupled to the motor by a rotating lever mechanism or wobble plate, inducing an oscillating translational movement of the sleeve in response to a rotation of the output shaft. The motor is preferably an electrical device coupled to an external power source by wires that are attached to a control system at the handle.

FIG. 22 shows an embodiment wherein the irrigation lumen 2222 contains the cutting sleeve 2244. Cutting sleeve 2244 has a cutting blade 2245 integrally formed at its distal end. FIG. 23 shows an alternative embodiment, wherein the irrigation lumen 2322 does not contain the cutting sleeve. An aspiration lumen 2224, 2324 is also provided. The aspiration line may be directly coupled to an aspiration pump; the irrigation lumen may be directly coupled to an irrigation pump.

The procedure for goniectomy with the goniectomy cutting probe is similar to the goniectomy procedure discussed for the goniectomy cauterization probe. However, rather than cauterizing the trabecular meshwork, the tissue is cut using a rotatable blade or cut in a guillotine fashion, and subsequently aspirated. In a preferred embodiment, a substantial portion, preferably at least half, of the trabecular meshwork is removed.

Goniectomy Laser Probe.

A laser probe 2400, as shown in FIGS. 24*a* and 24*b*, is provided to ablate the trabecular meshwork. The probe 2400 comprises a handle 2405 and a probe tip 2410. The handle 2405 is sized and configured to fit completely and comfortably within a hand. It will be understood that the handle 2405 may be formed from a variety of materials, including plastics, and may be designed in a variety of shapes. Generally, it will be preferred that a convenient shape for gripping, such as a cylindrical shape, be provided. The main body of the handle 2405 comprises a plastic housing within which a laser system is contained. The plastic housing is provided to enable easy manipulation of the handle 2405 by the user. The laser is preferably an excimer laser.

FIG. 24*a* shows an embodiment wherein the laser source is contained within the probe, but rather within the control system. A fiber is provided to direct the light energy from the source to the proximal end of the probe tip. The laser radiation is generated in close proximity to the eye, so that relatively little laser light is lost during transmission.

FIG. 24*b* shows an embodiment wherein the laser source is not contained within the probe. The source may include a longitudinal flashlamp. A fiber is provided to direct the light energy from the source to the proximal end of the probe tip.

The probe tip 2410 is connected to the main body 2405. The probe tip comprises a footplate to protect the outer wall of Schlemm's canal, such that only the tissue of the trabecular meshwork is cauterized. The footplate also is used to penetrate the trabecular meshwork and serves as a guide in Schlemm's canal. In general, the probe tip 2410 is straight or curved.

Figure 25:
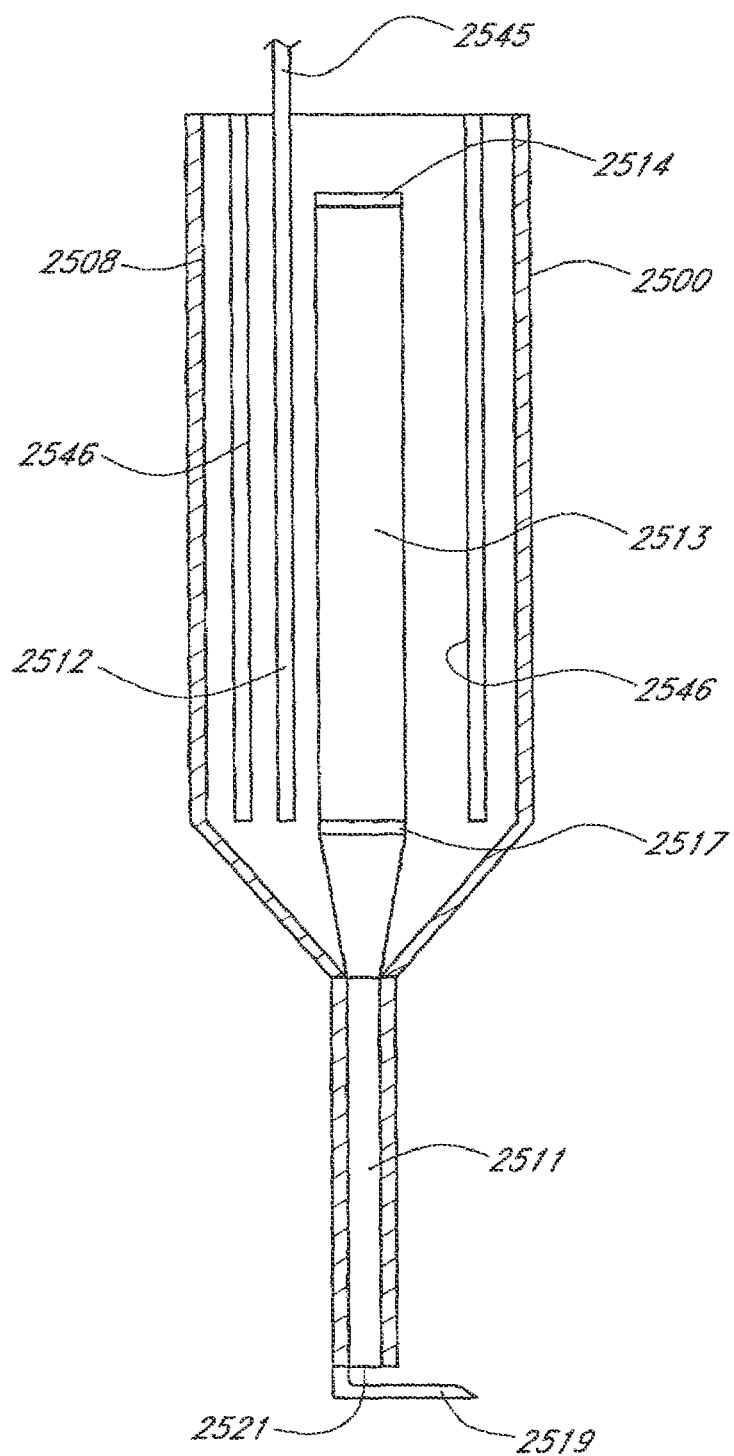

FIG. 25 shows a detailed view of FIG. 24*a*. The handle includes a reflective tube 2508 which has a mirrored inside surface. An Er:YAG rod 2513 is located along the axis of the tube 2508. The pump for the laser light source is preferably a high pressure flashtube 2512 or a similar suitable light source which is located adjacent the rod 2513 within the reflective tube 2508. The flashtube 2512 produces very brief, intense flashes of light, there being approximately 10 to 100 pulses per second.

Er:YAG rods generate an output wavelength of approximately 2.94 microns. Use of an erbium doped laser, such as an Er:YAG laser, is advantageous because it requires less power to ablate the eye tissue than do the Nd:YAG and Holmium:YAG lasers of the prior art. Preferably the Er:YAG laser has a pulse repetition rate of 5 to 100 Hz, a pulse duration of 250 µs to 300 µs, and a pulse energy of 10 to 14 mJ per pulse. Using an Er:YAG laser at the above parameters limits the thermal damage of surrounding tissue to a depth of 5 to 50 microns. By reducing the thermal damage of surrounding tissue, the amount of scar tissue buildup caused by the laser is minimal. Thus, the likelihood that the passageway will become blocked with scar tissue is reduced, and the likelihood that the procedure will need to be repeated is reduced.

The reflective inner surface 2546 of the tube 2508 serves to reflect light from the flashlamp 2512 to the rod 2513. Reflection of the light by the cylindrical mirror focuses as much light as possible toward the rod 2513. This results in efficient coupling between the light source 2512 and the laser rod 2513. Thus, essentially all light generated in the flashtube 2512 is absorbed by the laser rod 2513.

The rod 2513 has a totally reflective mirror 2514 and output mirror 2517 at its two ends. The mirror 2514 at the proximal end of the rod 2513 provides 100% reflection of light back to the rod 2513. At the remote end of the rod 2513, the output mirror 2517 provides less than 100% reflection. Thus, while most of the light energy directed toward the output mirror 2517 of the rod 2513 is reflected back into the rod 2513, intensifying the beam, some of the waves of energy pass through the output mirror 2517 and into the transmission system 2511 for conducting it toward the probe tip 2515. A reflective coating on the end of the laser rod 2513 may be used to supplement or replace the mirrors 2517, 2514.

The mirrors 2517, 2514 on either end of the rod form a resonator. Radiation that is directed straight along the axis of the rod 2513 bounces back and forth between the mirrors 2517, 2514 and builds a strong oscillation. Radiation is coupled out through the partially transparent mirror 2517.

The transmission system 251 is preferably an optical fiber. Preferably, a sapphire or fused silica fiber will be used with the laser, contained within the handle. A germanium oxide Type IV fiber is also suitable for carrying erbium laser light with reduced attenuation. It is also possible to deliver laser light through hollow waveguides. Such waveguides often include multi-layer dielectric coatings to enhance transmission.

Figure 26:
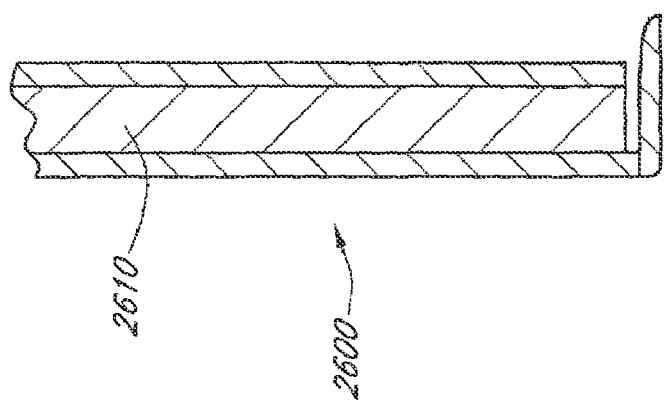
FIG. 26 is a cross sectional schematic diagram of the laser goniectomy probe of FIG. 24b.

FIG. 26 shows a detailed view of one embodiment of a probe tip 2600, in which the fiber 2610 is centrally located within the probe tip 2600.

Figure 27:
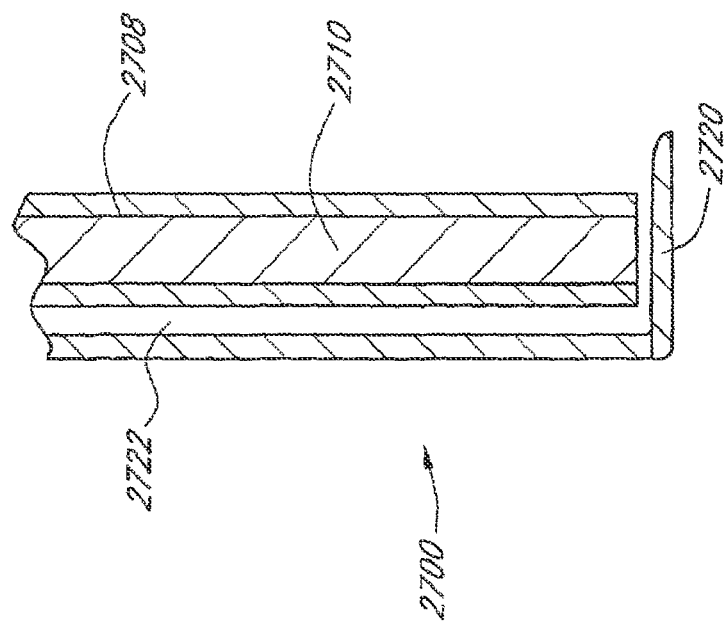
FIG. 27 is a cross sectional schematic diagram of the laser goniectomy probe of FIG. 24b.

Alternatively, the probe tip may be hollow, forming an aspiration/irrigation lumen (not shown). The lumen extends the entire length of the probe. Alternatively, as shown in FIG. 27, the lumen 2722 may extend adjacent the probe tip 2710. The aspiration lumen 2722 communicates with a vacuum source for withdrawal of emulsified material through an aperture or aspiration port. During use, the vacuum source can be employed to aspirate material which has been fragmented or ablated by the pulsed laser light. The vacuum source can also be used to draw the tissue into close proximity with the delivery end of the probe thereby facilitating its destruction. Fluid introduced through the lumen, chamber, and aperture can provide for flushing of the site and replacement of lost volume due to removal of the emulsified material.

The probe is inserted under direct vision to ablate the trabecular meshwork for use in treating glaucoma, thus obtaining a free flow of aqueous from the anterior chamber into Schlemm's canal and through the collector channels. The end of the probe is inserted through a relatively small incision in the eye, and can be maneuvered very close to the tissue to be emulsified.

The procedure is similar to the goniectomy procedure previously discussed with reference to the goniectomy cauterization probe. The surgeon visualizes the trabecular meshwork under direct microscopy and engages the superficial layers of the meshwork at the midpoint of the trabecular band, by placing the tissue between the end 2521 of the fiber 2511 and the probe tip (footplate) 2519. Once inserted, the fiber 2511 is positioned to focus laser energy directly on the trabecular meshwork. The probe tip 2519 absorbs any laser energy which is not absorbed by the trabecular meshwork, thus protecting Schlemm's canal from damage. Light is transmitted to and through the probe, and the tissue is ablated. The area may be irrigated and aspirated, removing the tissue from the eye. In a preferred embodiment, a substantial portion, preferably at least half, of the trabecular meshwork is removed. After treatment, the probe is readily withdrawn from the eye. Leakage may be stopped using a suture and burying the knot.

Laser treatment with an Er:YAG laser is advantageous because as wavelength increases, contiguous thermal effects decrease. In the visible portion of the spectrum, water has minimal absorption. Above 2.1 µm however, this absorption increases to a level comparable to excimer lasers operating around 200 nm. This increase is quite rapid. A marked difference therefore exists between radiation at 2.79 µm and 2.94 µm. This confines the energy delivered to a smaller volume, allowing more ablation to occur at lower total energy levels and limiting contiguous thermal damage. Er:YAG lasers produce ablations with minimal amounts of contiguous thermal damage. Light in the infrared region has an additional advantage over ultraviolet radiation in that it is not known to have mutagenic or carcinogenic potential.

Due to the large absorption band of the water at the wavelength of the erbium laser, no formation of sticky material on the probe tip takes place, which can be a serious problem at other wavelengths.

Schlemmectomy Cauterization Probe.

Figure 28:
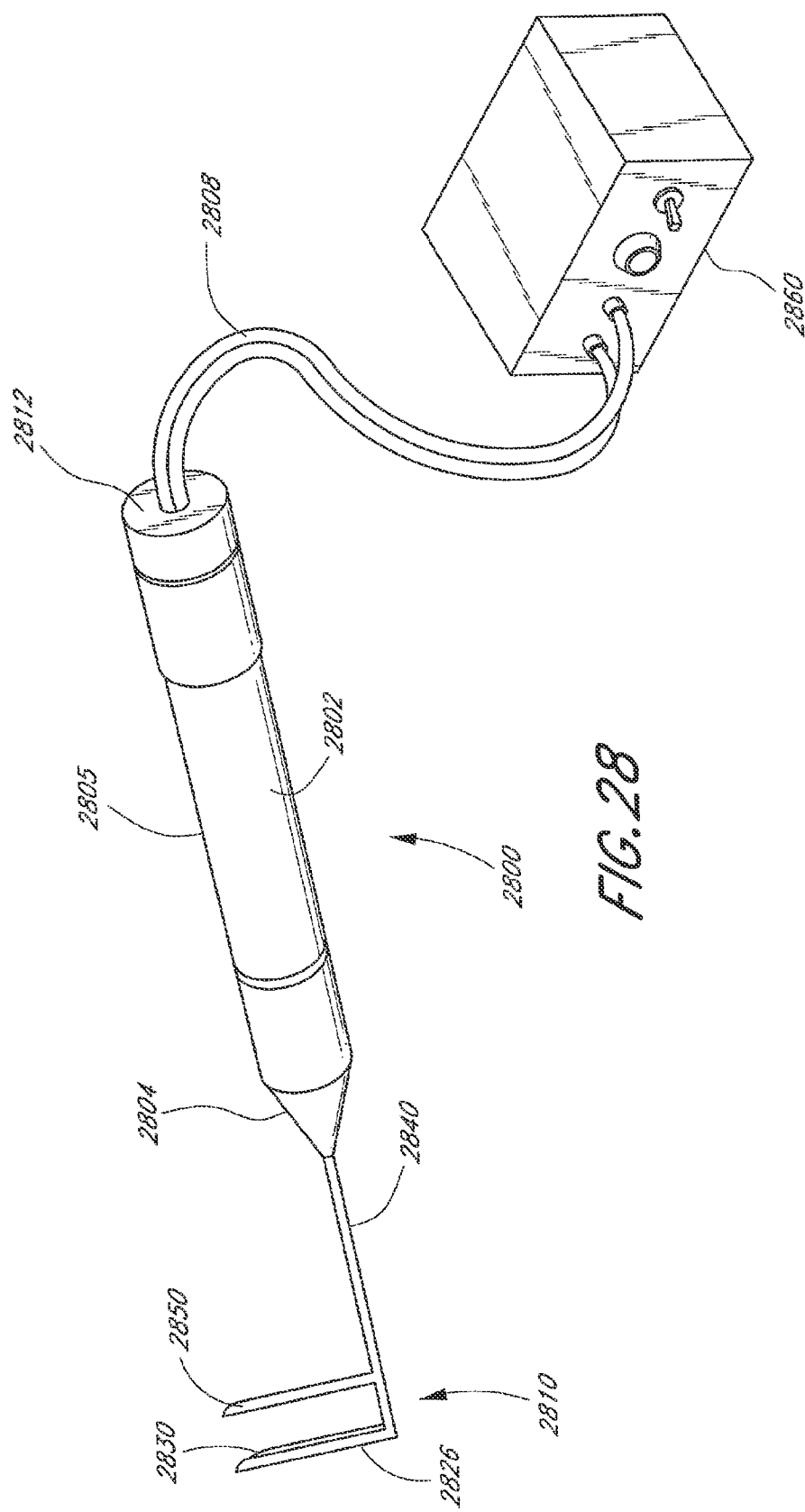
FIG. 28 is a perspective view which shows a Schlemmectomy probe of a preferred embodiment.

Schlemmectomy is a new surgical procedure, similar to trabeculotomy. However, in a schlemmectomy, procedure, disrupted tissue is removed using a schlemmectomy cauterization probe. FIG. 28 illustrates a probe 2800 in accordance with this invention for removal of the trabecular meshwork, using a cautery element 2830 on a probe similar to a traditional trabeculotome, such as Harm's trabeculotome. The probe uses both cautery and mechanical disruption to ablate the fibers of the trabecular meshwork, leaving a patent open Schlemm's canal.

The probe 2800 comprises a handle 2805 and a probe tip 2810. The proximal end of the handle is adapted for mating with a connector 2812 to the output terminals of an energy source 2860.

The probe also includes electrical leads 2934 (FIG. 29), a power cable 2808, preferably a coaxial cable, and an actuator. These components extend from the handle 2805, through an electrical lead lumen 2932 (FIG. 29) in the probe shaft 2805, to the corresponding components of the probe 2800 disposed on the distal end. The proximal ends of the cables and lumens connect to the corresponding connectors that extend from the distal end of the probe handle 2805.

FIGS. 29a-c illustrate one probe tip configuration. The probe tip 2910 comprises two parallel arms 2920, 2950. The probe tip 2910 comprises an electrode 2930, which will be described in further detail below, disposed on the lower arm 2920. The probe tip 2910 comprises an electrical lead lumen 2932 which extends the length of the probe tip 2910 from the electrode 2930 through the cylindrical body 2802 to the connector of the probe handle 2812. (FIG. 28)

Figure 30:
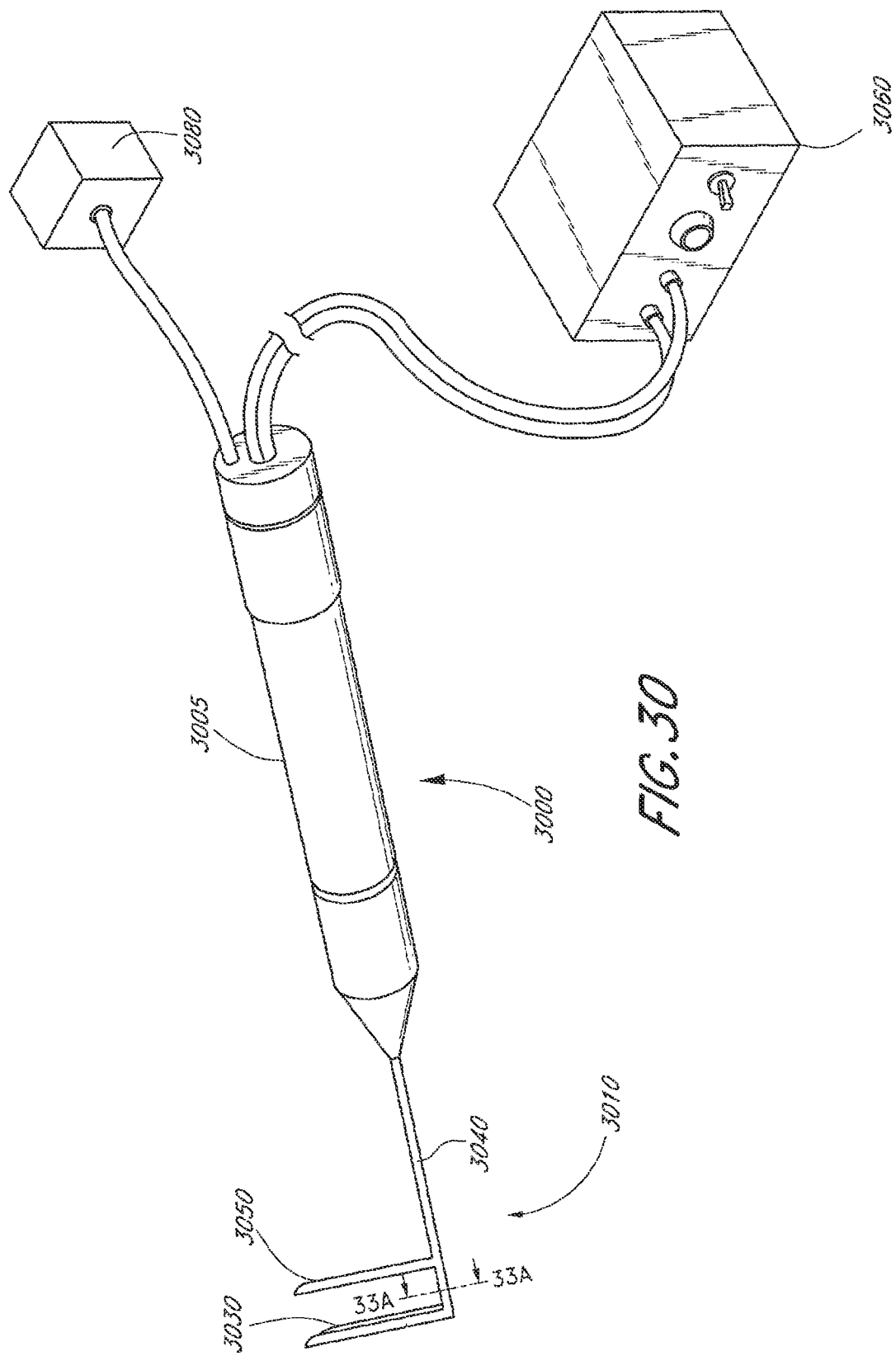
FIG. 30 is a perspective view of an alternative preferred embodiment of the probe of FIG. 28.

FIG. 30 shows a preferred embodiment of a probe 3000. The probe of FIG. 30 is similar to the probe of FIG. 28, except that probe 3000 further comprises irrigation means. Irrigation may be provided by an irrigation pump 3080 or hydrostatic pressure from a balanced salt solution bottle and tubing.

Figure 31A:
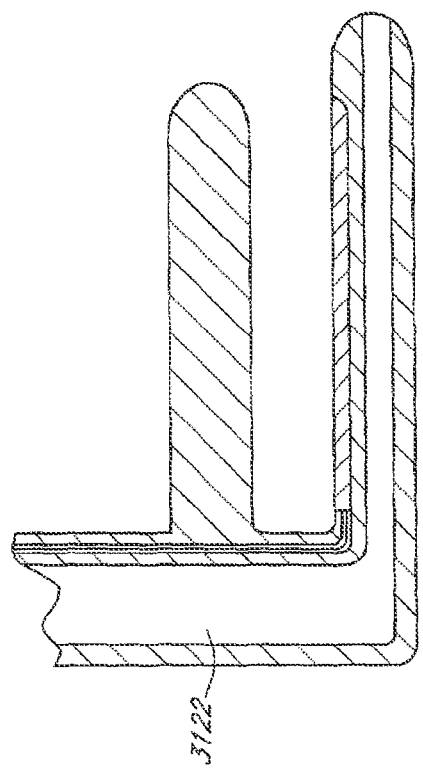
FIGS. 31 a,b,c are detailed views of the probe tip of FIG. 30.
Figure 31B:
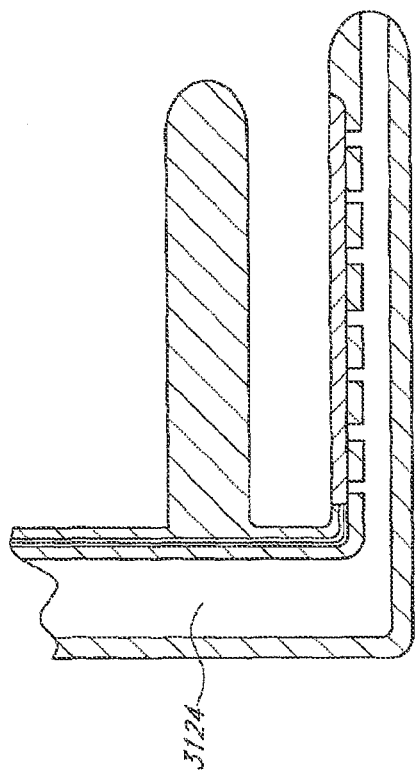
Figure 31C:
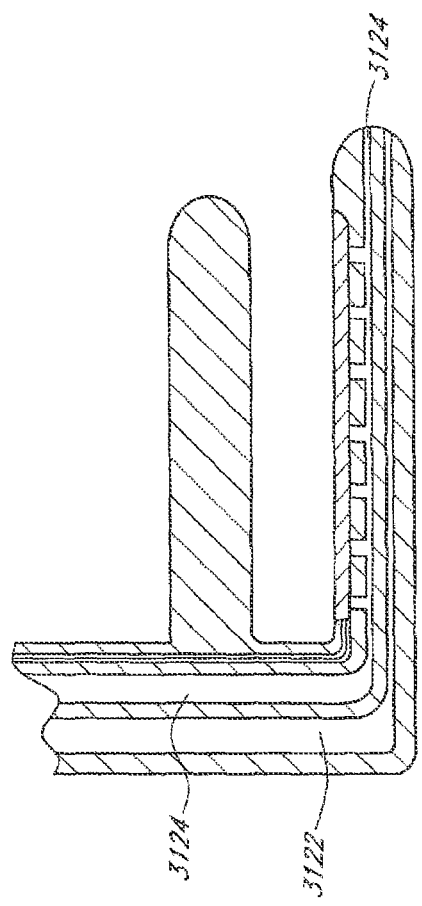

In a preferred embodiment, as shown in FIG. 31a, the irrigation lumen 3122 is situated at the end of the probe. Irrigation under pressure flushes blood from the eye and expands Schlemm's canal and the anterior chamber, providing more room for the procedure. Alternatively, lumen 3122 provides for aspiration by connecting the lumen to an aspiration pump. Aspiration ports may be provided equidistantly along the length of the cauterizing element of the trabeculotome, as shown in FIG. 31b. In an embodiment, as shown in FIG. 31c, two lumens are provided, an irrigation lumen 3122 and an aspiration lumen 3124. Two separate lumens provide for simultaneous irrigation and aspiration.

With reference to the schlemmectomy probes of FIGS. 28 and 30, the handle 2805, 3005 may be made of an electrically insulating polymeric material, configured in a pencil-shape form having a cylindrical body region 2802, 3002 and a tapered forward region 2804, 3004. Although a pencil-shape configuration is preferred, it is noted that any configuration of the handle 2805, 3005 which is easily, comfortably and conveniently grasped by the operator will also be suitable and is considered to be within the scope of the present invention.

The probe tip 2810, 3010 is connected to the main body of the handle 2805, 3005. The cautery element 2830, 3030 at the distal end of the probe tip 2810, 3010 can have a variety of configurations.

The tip 2810, 3010 may be any material, such as titanium, brass, nickel, aluminum, stainless steel, other types of steels, or alloys. Alternatively, non-metallic substances may also be used, such as certain plastics. The tip may be conductive or non-conductive, depending on the specific embodiment, as will be discussed.

Figure 32A:
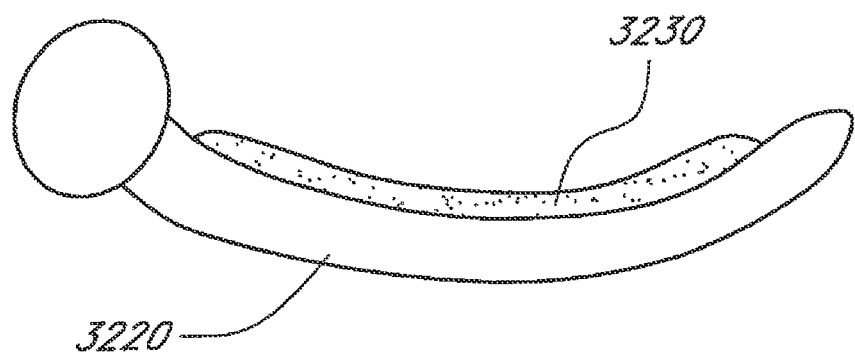
FIGS. 32a,b are detailed views which show the probe tip of the probe of FIG. 30.
Figure 32B:
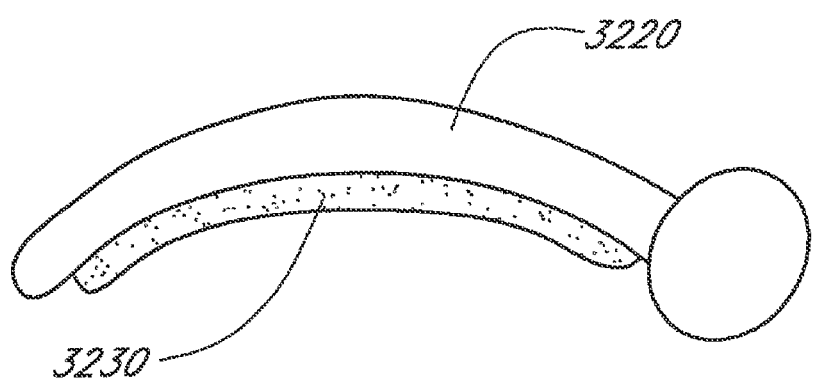

FIGS. 32a and 32b show alternative distal probe tip configurations, wherein the second electrode 3230 extends along the entire length of the first electrode 3220. The probe tip 3210 may be curved to better maneuver within the anatomy of the eye. The malleable probe tips can be configured as straight, angled or curved, for example, which provides for optimal access to specific anatomy and pathology. Unique tip designs improve tactile feedback for optimal control and access, and provide for improved tissue visualization with greatly reduced bubbling or charring.

Referring again to the probes of FIGS. 28 and 30, the probe tip 2810, 3010 comprises an electrode or cautery element 2830, 3030, suitable for cautery, as known to those of skill in the art. Various electrode configurations and shapes may be suitable. The cautery element 2830, 3030 is any electrode that may provide ablation or cauterization of tissue, such as a RF electrode, an ultrasound transducer, or any other suitable electrode. Alternatively, or in addition to the RF electrode variations, the cautery element may also include other cautery energy sources or sinks, and particularly may include a thermal conductor. Examples of suitable thermal conductor arrangements include a metallic element which may, for example, be constructed as previously described. In the thermal conductor embodiment such a metallic element would be generally resistively heated in a closed loop circuit internal to the probe, or conductively heated by a heat source coupled to the thermal conductor.

The electrode 2830, 3030 may be provided on the inner surface of the tip. Alternatively, the electrode 2830, 3030 may be embedded in a sheath of a tube. Insulation may be provided around the cautery element so that other areas of the eye are not affected by the cauterization. A sleeve shield or a non-conductive layer may also be provided on the probe tip to expose only a selected portion of the electrode. The sleeve preferably has sufficient thickness to prevent both current flow and capacitance coupling with the tissue.

The cautery element can be made of a number of different materials including, but not limited to stainless steel, platinum, other noble metals, and the like. The electrode can also be made of a memory metal, such as nickel titanium. The electrode can also be made of composite construction, whereby different sections are constructed from different materials.

In a preferred embodiment of an RF electrode, the electrode system is bipolar. In a bipolar system, two electrodes of reversed polarity are located on the probe tip and RF energy bridges the electrodes. Additionally, any number of pairs of electrodes may be provided on the probe tip.

In an alternative RF electrode embodiment, the electrode system is monopolar. In a monopolar system, the system comprises a single electrode and a contact plate. The contact plate is attached to the surface of the human body. The contact plate is further connected to the return terminal of the power source via a lead wire. Voltages of reverse polarity are applied to the electrode and the contact plate.

Figure 33B:
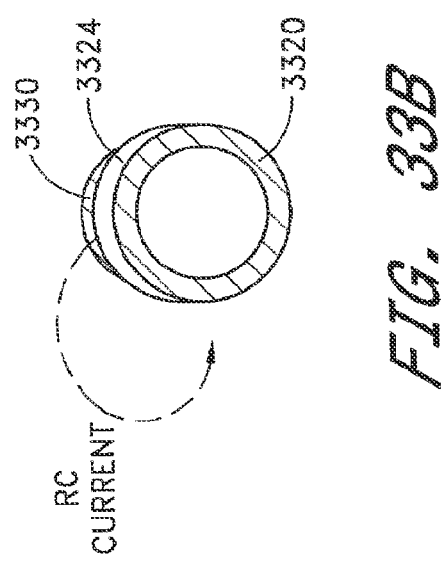
FIG. 33b is a cross-sectional schematic diagram which shows the probe tip of the probe of FIG. 30.
Figure 33A:
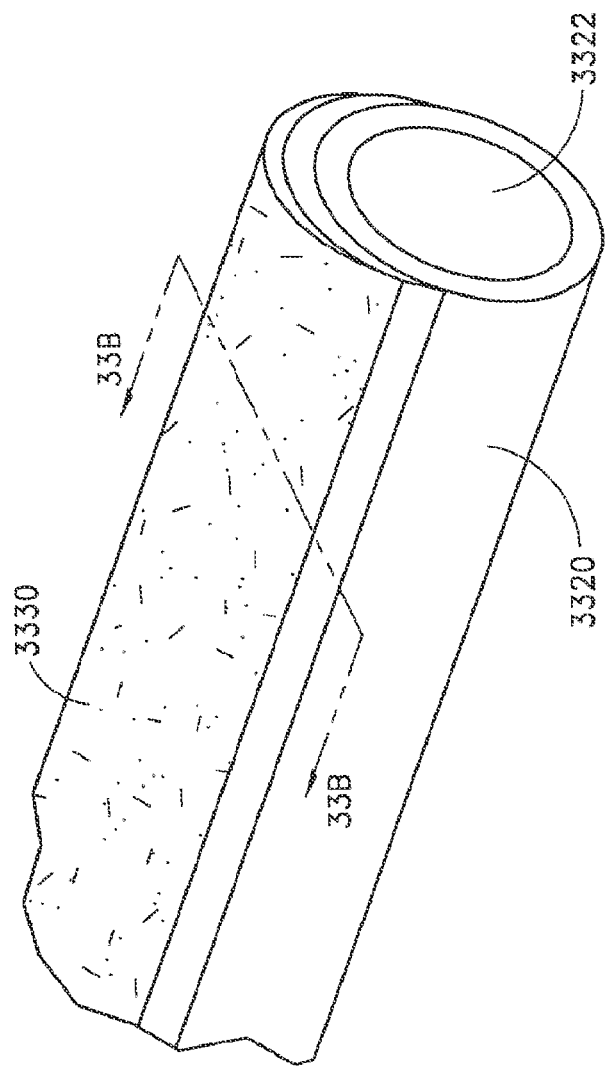
FIG. 33a is a detailed view which shows the probe tip of the probe of FIG. 30.

In a preferred embodiment, as shown in FIGS. 33a and 33b, an electrode assembly of a bipolar probe includes one electrode 3320 made from a stainless steel 20 gauge hollow needle and a second electrode 3330 formed as a layer of electrically conductive material (such as silver or nickel) deposited over and adhered to an exterior surface of the needle electrode. A thin electrical insulator 3324 separates the electrodes 3320, 3330, along their lengths to avoid short circuiting.

The electrodes 3320, 3330 extend along a longitudinal axis 3372 of the instrument from a proximal region at which bipolar electrical power is applied to a distal region of the electrode assembly.

In a preferred embodiment, the second electrode 3330 extends over a limited portion of the circumference of the first electrode 3320, rather than entirely around the first electrode 3320. Current flows from the relatively small portion of the circumference of the second electrode 3330 where heat is generated in the adjacent tissue, and into the layer surface of the first electrode 3320, where little heat is generated. This limits the area in the body that receives dense current, and provides the operator with a high degree of control as to where the current is applied. The second electrode 3330 extends over an arc of approximately one quarter of the circumference of the first electrode. The second electrode 3330 is disposed symmetrically about an axis 3372.

In a preferred embodiment, the first electrode 3320 has a central passage 3322 that is open at the distal region, providing for irrigation. The irrigation lumen 3322 extends from the distal end of the probe tip, through the probe handle, to the connector, providing for irrigation capability.

Figure 34B:
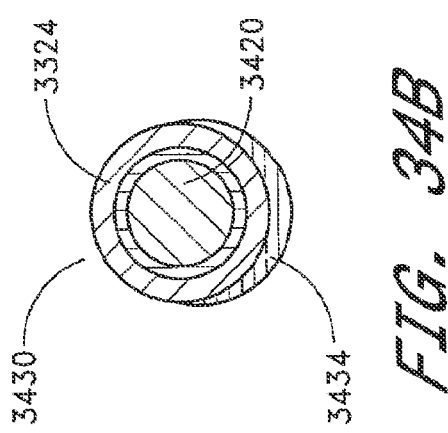
FIG. 34b is a cross-sectional schematic diagram which shows the probe tip of the probe of FIG. 30.
Figure 34A:
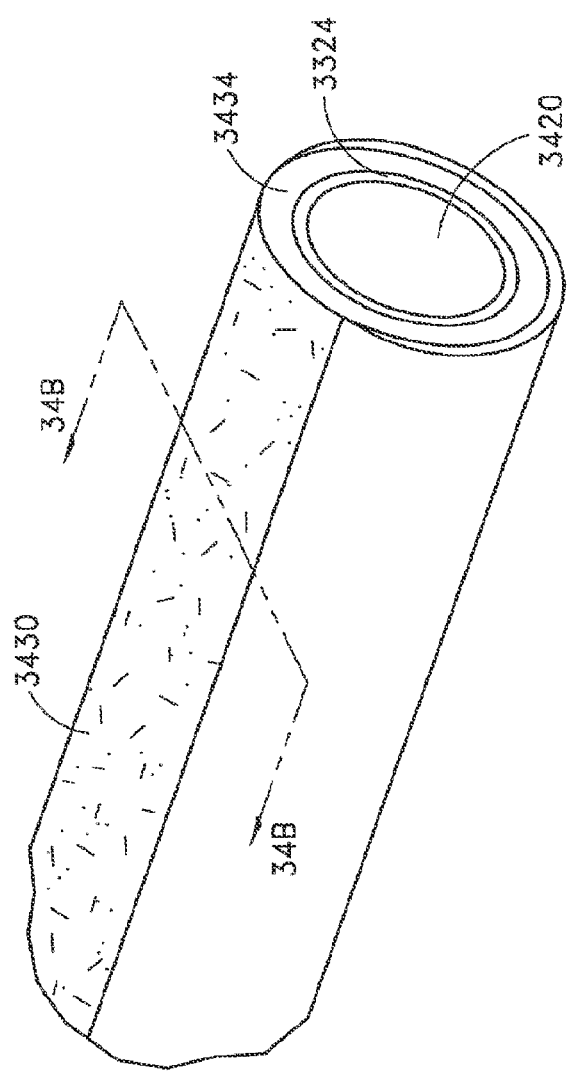
FIG. 34a is a detailed view which shows the probe tip of the probe of FIG. 30.

FIG. 34 shows an alternative embodiment, wherein the electrode assembly includes a central or axial electrode 3420 formed by a solid cylindrical metal member, and an elongate hollow outer electrode 3430 formed by a cylindrical metal tube member, which is coaxially positioned around the central electrode. The cylindrical outer surface of electrode 3430 forms the circumferential surface of the probe. The outer electrode 3430 is preferably made of stainless steel or other corrosive resistant, conductive material for strength as well as conductivity. The inner electrode 3420 may be made of copper, but less conductive materials may also be employed. The coaxial relationship and spacing between the electrodes, as well as their electrical isolation from one another, is provided by a tubular sleeve 3424 of an electrically insulating material between the electrode, completing the probe assembly. An additional layer of insulation 3434 may be provided on outer electrode 3430 to expose only a limited portion of the electrode to concentrate RF energy at the limited exposed region.

Alternatively, one or more regions of insulating area 3434 may be removed at any suitable location along the axis to expose a region of electrode 3430. Cauterization would then occur at the exposed region. The circumferential extent of the second electrode 3430 can be further limited, depending on the degree of control desired over the size of the area to which current is applied.

In an alternative embodiment as shown in FIGS. 35a and 35b, the active region of a bipolar electrode probe assembly is formed by a hollow metal tube 3515 having a substantially semi-cylindrical sleeve 3524 on tube 3515. The metallic tube 3515 is not an electrode and is provided only for the strength of the probe assembly. The tip supports two cautery elements 3520, 3530. Each of the elements 3520, 3530 is connected to electrical leads, which extend through the hollow interior of the tip 3510 to a supporting insulative handle where it is coupled by appropriate means with a power source in the manner previously described.

The probe is connected to a low voltage RF power source via a power cord that mates with the handle. The source may be a high frequency, bipolar power supply, preferably, a solid state unit having a bipolar output continuously adjustable between minimum and maximum power settings. The source is activated by an on/off switch, which may comprise a foot pedal, or a button on the probe or interface. The source provides a relatively low bipolar output voltage. A low voltage source is preferred to avoid arcing between the electrode tips, which could damage the eye tissue. The RF generator is coupled to first and second electrodes to apply a biologically safe voltage to the surgical site. This probe has the advantage of cauterizing at both of the bipolar elements, each of which has a limited, RF current concentration area.

Delivery of energy to the tissue is commenced once the cautery element is positioned at the desired location. Energy is typically delivered to the cautery element via electrical conductor leads. The energy source preferably provides RF energy, but is not limited to RF and can include microwave, electrical, ultrasonic, coherent and incoherent light thermal transfer and resistance heating or other forms of energy, as known to those of skill in the art.

The cautery actuator may include a monitoring circuit 1744 and a control circuit 1746 (FIG. 17) which together use either the electrical parameters of the RF circuit or tissue parameters such as temperature in a feedback control loop to drive current through the electrode element during cauterization. Feedback control systems can be used to obtain the desired degree of heating by maintaining the selected sight at a desired temperature for a desired time. A sensor, such as a thermocouple may be used to monitor temperature in a feedback loop. Where a plurality of cautery elements or electrodes are used, switching capability may be provided to multiplex the RF current source between the various elements or electrodes.

FIG. 17 shows the monitor circuit 1744, which desirably communicates with one or more sensors (e.g., temperature) 1740 which monitor the operation of the cautery element 1730. The control circuit 1746 may be connected to the monitoring circuit 1744 and to the current source in order to adjust the output level of the current driving the cautery element 1730 based upon the sensed condition (e.g. upon the relationship between the monitored temperature and a predetermined temperature set point).

Circuitry, software and feedback to a controller, which result in full process control, may be used to change (i) power—including RF, incoherent light, microwave, ultrasound, and the like, (ii) the duty cycle, (iii) monopolar or bipolar energy delivery, (iv) fluid (electrolyte solution delivery, flow rate and pressure) and (v) determine when ablation is completed through time, temperature and/or impedance.

In a preferred embodiment, a bipolar electrode is part of a circuit that includes the RF signal generator, connecting cables, probe tip for insertion into the eye, a grounding electrode attached to the probe and a return cable that connects the grounding electrode to the RF generator completing the circuit. Because such a RF electrode is a relatively good conductor, the electrode itself does not heat up. The tissues that the electrode comes in contact with heat up in response to current passing from the electrode through the tissues. The tissue heats up because it is a relatively poor conductor as compared to the rest of the circuit. It is when the tissues heat up as a result of molecular friction, that heat is then conducted back to the electrode itself. At that point, a thermocouple senses the increase in temperature and supplies that information to the RF generator so that the feedback mechanism can attenuate the energy delivered in order to attain temperature control.

It may also be advantageous to regulate RF delivery through both temperature and impedance monitoring. It may also be advantageous to monitor irrigation fluid flow to maintain clarity at the site. There is also an opportunity for synergy between RF and irrigation fluid delivery to the surgical site to provide, for example, a greater level of control of temperatures at the site.

The controller may include an RF generator, temperature profile, temperature regulator, temperature monitor, surgical instrument, impedance monitor, impedance regulator, pump, flow regulator and flow monitor.

The RF generator may be capable of delivering monopolar or bipolar power to the probe. The probe is positioned at the surgical site. The impedance monitor obtains impedance measurements by, for example, measuring current and voltage and performing a RMS calculation. The measurements of the impedance monitor are delivered to the impedance regulator. The impedance regulator performs several functions. Generally the impedance regulator keeps the impedance levels within acceptable limits by controlling the power supplied by the RF generator. In one embodiment of the current invention the impedance regulator can control the flow regulator to deliver more or less irrigation fluid to the surgical site.

To maintain the appropriate temperature for cauterizing tissue, the distal tip of the probe may also be equipped with a thermocouple 1740. Temperature feedback, in combination with a timing device, permits a precise degree of cautery to be delivered, obtaining the desired effect without causing any intraocular heating. The heating effect on tissue may be mitigated with a viscoelastic agent to deepen the anterior chamber.

Referring to FIG. 17, the temperature monitor 1744 may include one or more types of temperature sensors, e.g. thermocouples, thermistors, resistive temperature device (RID), infrared detectors, etc.

Suitable shapes for the thermocouple include, but are not limited to, a loop, an oval loop, a "T" configuration, an "S" configuration, a hook configuration or a spherical ball configuration. These shapes provide more surface area for the thermocouple without lengthening the thermocouple. These thermocouples, with more exposed area than a straight thermocouple, are believed to have better accuracy and response time. The thermocouple is attached by a fastener. The fastener may be a bead of adhesive, such as, but not limited to, epoxies, cyanoacetate adhesives, silicone adhesives, flexible adhesives, etc. It may also be desirable to provide multiple thermocouples at different locations and compare their operating parameters (e.g. response times, etc.), which may provide useful information to allow certain such variables to be filtered and thereby calculate an accurate temperature at the thermocouple location.

The output of the temperature monitor 1744 is delivered to the temperature regulator 1746. The temperature regulator 1746 may control both the RF generator 1760 and the flow regulator. When, for example, temperatures have increased beyond an acceptable limit, power supplied by the RF generator to the surgical instrument may be reduced. Alternately, the temperature regulator may cause the flow regulator to increase irrigation fluid, thereby decreasing the temperature at the surgical site. Conversely, the temperature regulator can interface with either the RF generator or the flow regulator when measured temperatures do not match the required temperatures. The flow regulator interfaces with the pump to control the volume of irrigation fluid delivered to the surgical site.

The procedure for performing a Schlemmectomy with the probe of the present invention is similar to a traditional trabeculotomy procedure, as previously described. The surgeon preferably sits on the temporal side of the operating room table utilizing the operating microscope. An infrotemporal formix based conjunctival flap is made and the conjunctive and Tenons capsule are mobilized posteriorly. A triangular flap is made and the superficial flab is mobilized into the cornea. A radial incision is made over the canal of Schlemm, thus creating an entrance into the canal. Vanua scissors are preferably introduced into the Schlemm's canal, opening the canal for approximately 1 mm on either side. A clear corneal parenthesis is performed and the anterior chamber is deepened, preferably with Haelon GV. The probe is introduced into Schlemm's canal inferiorly. The instrument is now aligned such that the cauterization element faces into the deepened anterior chamber. Alternatively, the cauterization surface faces the trabecular meshwork and is activated by the foot switch at the time of the rotation of the probe into the anterior chamber. The foot switch may then be used to activate cauterization. Aspiration and irrigation may also be activated using the foot switch. The trabeculotome is slowly rotated into the anterior chamber and when the blade of the trabeculotome is seen in the anterior chamber, the cautery (and aspiration and/or irrigation) are deactivated. The superior aspect of Schlemm's canal may be entered with a trabeculotome having the opposite curvature. Following the same steps, more of the trabecular meshwork is removed. In a preferred embodiment, a substantial portion, preferably at least half, of the trabecular meshwork is removed. After removing the trabeculotome, the superficial trabeculotomy flap is sutured closed using sutures.

Radiowave surgery uses high frequency radio waves instead of heat to cut and coagulate tissue without the burning effect that is common with traditional electrosurgical devices and cautery equipment. The resistance of tissue to the spread of radio wave energy produces heat within the cell, causing the water within the cell to volatilize and destroy the cell without damaging other cellular layers.

While particular forms of the invention have been described, it will be apparent that various modifications can be made without departing from the spirit and scope of the invention. Accordingly, it is not intended that the invention be limited, except as by the appended claims.

What is claimed is:

1. A device for forming an opening in the trabecular meshwork of the eye of a subject, said device comprising:
    an elongate probe having a distal end that is insertable into the anterior chamber of the eye;
    a member extending from the distal end of the elongate probe, said member having opposing upper and lower sides; and
    a cutting or ablating apparatus is located adjacent to the upper side of the member;
    said member being insertable, while the elongate shaft extends through the anterior chamber of the eye, into the Schlemm's canal such that the member is advanceable through a portion of Schlem's canal with the cutting or ablating apparatus cutting or ablating trabecular meshwork tissue as the member is being so advanced.

2. A device according to claim 1 wherein the cutting or ablating apparatus forms an elongate opening or slit in the trabecular meshwork as the member is being advanced through a portion of Schlem's canal.

3. A device according to claim 1 wherein the member has a tip that is configured to penetrate through the trabecular meshwork as it is being inserted into Schlemm's canal.

4. A device according to claim 1 wherein the member extends at an angle relative to the elongate probe.

5. A device according to claim 4 wherein the member is substantially perpendicular to the elongate probe.

6. A device according to claim 1 further comprising an aspiration opening.

7. A device according to claim 1 further comprising an irrigation opening.

8. A device according to claim 1 further comprising an aspiration opening and an irrigation opening.

9. A device according to claim 1 further comprising a second member that extends from the elongate probe and is generally parallel to the member on whose upper surface the cutting or ablating apparatus is located.

10. A device according to claim 9 wherein the second member is juxtaposed to and spaced away from the upper surface the cutting or ablating apparatus is located.

11. A device according to claim 1 wherein the cutting or ablating apparatus comprises an electrode.

12. A device according to claim 1 wherein the cutting or ablating apparatus comprises a radiofrequency electrode.

13. A device according to claim 1 wherein the cutting or ablating apparatus comprises a cutting blade.

14. A device according to claim 1 wherein the cutting or ablating apparatus comprises a laser.

15. A device according to claim 1 wherein the cutting or ablating apparatus emits sonic energy.

16. A device according to claim 1 wherein the cutting or ablating apparatus emits acoustic energy.

17. A device according to claim 1 wherein the cutting or ablating apparatus emits ultrasonic energy.

18. A method for improving drainage of fluid from the anterior chamber of an eye of a subject, said method comprising the steps of:
A) preparing a glaucoma treatment device that comprises i) an elongate probe having a distal end that is insertable into the anterior chamber of the eye, ii) a member extending from the distal end of the elongate probe, said member having opposing upper and lower sides and iii) a cutting or ablating apparatus located adjacent to the upper side of the member;
B) inserting a distal portion of the elongate probe into the anterior chamber of the subject's eye;
C) with the distal portion of the probe positioned in the anterior chamber of the eye, positioning the member in Schlemm's canal with the cutting or ablating apparatus positioned to cut or ablate tissue of the trabecular meshwork; and
D) advancing the member through a segment of Schlem's canal such that the cutting or ablating apparatus cuts or ablates a segment of the trabecular meshwork thereby forming an opening through which fluid may drain from the anterior chamber into Schlemm's canal.

19. A method according to claim 18 wherein the device provided in Step A further comprises an aspiration opening through which matter may be aspirated and wherein the method further comprises the step of aspirating matter from the eye through said aspiration opening.

20. A method according to claim 19 wherein the matter aspirated through said aspiration opening comprises tissue that has been severed from the trabecular meshwork during performance of Step D.

21. A method according to claim 18 wherein the device further comprises an irrigation opening through which fluid may be infused and wherein the method further comprises the step of infusing a fluid into the eye through said irrigation opening.

22. A method according to claim 18 wherein the device further comprises an irrigation opening through which fluid may be infused and an aspiration opening through which fluid may be aspirated, and wherein the method further comprises the step of infusing a fluid into the eye through said irrigation opening and the step of aspirating matter from the eye through said aspiration opening.

23. A method according to claim 18 wherein the device is moved such that the member advances through a segment of Schlemm's canal during performance of Step D causing the cutting or ablating apparatus to form an elongate opening or slit in the trabecular meshwork.

24. A method according to claim 18 wherein the distal portion of the probe is inserted into the anterior chamber of the subject's eye through a corneal incision.

25. A method according to claim 18 further comprising the steps of:
(E) removing the device; and
(F) sealing the corneal incision.

26. A method according to claim 25 wherein the corneal incision is sealed by injecting a balanced salt solution into the corneal stroma.

27. A method according to claim 25 wherein the corneal incision is sealed by placement of a suture.

28. A method according to claim 18 wherein the device further comprises a second member that extends from the elongate probe parallel to the upper side of the member on which the cutting or ablating apparatus is located and in Step C the second member is positioned within the anterior chamber adjacent to the trabecular meshwork.

* * * * *